United States Patent
Li et al.

(10) Patent No.: US 11,753,524 B2
(45) Date of Patent: *Sep. 12, 2023

(54) OXYGEN SCAVENGERS, COMPOSITIONS COMPRISING THE SCAVENGERS, AND ARTICLES MADE FROM THE COMPOSITIONS

(71) Applicant: Plastipak Packaging, Inc., Plymouth, MI (US)

(72) Inventors: Shenshen Li, Park Rldge, IL (US); Matthew J. Dauzvardis, Manhattan, IL (US)

(73) Assignee: Plastipak Packaging, Inc., Plymouth, MI (US)

(*) Notice: Subject to any disclaimer, the term of this patent is extended or adjusted under 35 U.S.C. 154(b) by 0 days.

This patent is subject to a terminal disclaimer.

(21) Appl. No.: 17/379,955

(22) Filed: Jul. 19, 2021

(65) Prior Publication Data

US 2022/0073700 A1 Mar. 10, 2022

Related U.S. Application Data

(63) Continuation of application No. 16/508,282, filed on Jul. 10, 2019, now Pat. No. 11,066,536, which is a continuation of application No. 14/517,643, filed on Oct. 17, 2014, now Pat. No. 10,351,692.

(51) Int. Cl.
| | | |
|---|---|---|
| *C08K 5/20* | (2006.01) | |
| *B65D 81/24* | (2006.01) | |
| *C07C 233/78* | (2006.01) | |
| *C07C 235/42* | (2006.01) | |
| *C08G 63/91* | (2006.01) | |

(52) U.S. Cl.
CPC ............... *C08K 5/20* (2013.01); *B65D 81/24* (2013.01); *C07C 233/78* (2013.01); *C07C 235/42* (2013.01); *C08G 63/916* (2013.01)

(58) Field of Classification Search
CPC ....... C08K 5/20; C07C 233/78; C07C 235/42; C08G 63/916
See application file for complete search history.

(56) References Cited

U.S. PATENT DOCUMENTS

| | | |
|---|---|---|
| 2,841,591 A | 7/1958 | Prichard |
| 3,322,785 A | 5/1967 | Henry |
| 4,536,409 A | 8/1985 | Farrell et al. |
| 4,786,671 A | 11/1988 | Kress et al. |
| 5,021,515 A | 6/1991 | Cochran et al. |
| 5,034,252 A | 7/1991 | Nilsson et al. |
| 5,049,624 A | 9/1991 | Adams et al. |
| 5,075,362 A | 12/1991 | Hofeldt et al. |
| 5,116,547 A | 5/1992 | Tsukahara et al. |
| 5,159,005 A | 10/1992 | Frandsen et al. |
| 5,194,478 A | 3/1993 | Frandsen et al. |
| 5,211,875 A | 5/1993 | Speer et al. |
| 5,239,016 A | 8/1993 | Cochran et al. |
| 5,250,592 A | 10/1993 | Nesvadba |
| 5,281,360 A | 1/1994 | Hong et al. |
| 5,639,815 A | 6/1997 | Cochran et al. |
| 5,660,761 A | 8/1997 | Katsumoto et al. |
| 5,866,649 A | 2/1999 | Hong et al. |
| 5,955,527 A | 9/1999 | Cochran et al. |
| 6,057,013 A | 5/2000 | Ching et al. |
| 6,083,585 A | 7/2000 | Cahill et al. |
| 6,288,161 B1 | 9/2001 | Kim et al. |
| 6,610,234 B2 | 8/2003 | Akkapeddi et al. |
| 6,664,320 B1 | 12/2003 | Cai et al. |
| 6,780,916 B2 | 8/2004 | Tung et al. |
| 7,052,628 B2 | 5/2006 | Schmidt et al. |
| 7,097,890 B1 | 8/2006 | Ching et al. |
| 7,691,290 B2 | 4/2010 | Deshpande et al. |
| 7,879,930 B2 | 2/2011 | Liu |
| 7,994,245 B2 | 8/2011 | Deshpande et al. |
| 8,431,721 B2 | 4/2013 | Deshpande et al. |
| 8,450,398 B2 | 5/2013 | Deshpande |
| 8,721,920 B2 | 5/2014 | Deshpande et al. |
| 8,748,519 B2 | 6/2014 | Deshpande |
| 8,975,345 B2 | 3/2015 | Deshpande |
| 9,181,414 B2 | 11/2015 | Deshpande |
| 9,475,630 B2 | 10/2016 | Deshpande et al. |
| 2001/0008662 A1 | 7/2001 | Blinka et al. |
| 2003/0109643 A1 | 6/2003 | Ching et al. |
| 2003/0134966 A1 | 7/2003 | Kim et al. |
| 2004/0241468 A1 | 12/2004 | Otaki |
| 2005/0106343 A1 | 5/2005 | Kim et al. |
| 2006/0069197 A1 | 3/2006 | Tammaji et al. |

(Continued)

FOREIGN PATENT DOCUMENTS

| | | |
|---|---|---|
| AU | 2006214438 | 2/2006 |
| AU | 2008251476 A1 | 11/2008 |

(Continued)

OTHER PUBLICATIONS

Bandi, S. et al. (2005) "The mechanism of color generation in poly(ethylene terephthalate) / polyamide blends," *Polymer Degradation and Stability* 88: 341-348.

Böhme, H. et al. (1970) "Studies in phthalimidine series. 13. N-alpha halogenalkylcarboylic acid amides," *Pharmazie*, 25(5): 283-289.

Buhleier, E., et al. (1978) "2,6-Bis(aminomethyl)pyridine als Komplexligand und neues Kronenethersynthon," *Justus Liebigs Annalen der Chemie*, 4: 537-544. (Abstract).

Chen et al. (2007) "Efficient enhancement of DNA cleavage activity by introducing guanidinium groups into diiron(III) complex", *Bioorganic & Medicinal Chemistry Letters*, 18(1): 109-113.

(Continued)

*Primary Examiner* — Jane L Stanley
(74) *Attorney, Agent, or Firm* — Ballard Spahr LLP

(57) ABSTRACT

The disclosure relates to oxygen scavenging molecules, compositions, methods of making the compositions, articles prepared from the compositions, and methods of making the articles. This abstract is intended as a scanning tool for purposes of searching in the particular art and is not intended to be limiting of the present invention.

6 Claims, 1 Drawing Sheet

(56) References Cited

U.S. PATENT DOCUMENTS

| | | |
|---|---|---|
| 2006/0148957 A1 | 7/2006 | Stewart et al. |
| 2006/0180790 A1 | 8/2006 | Deshpande et al. |
| 2006/0182911 A1 | 8/2006 | Tammaji et al. |
| 2006/0247388 A1 | 11/2006 | Hale et al. |
| 2007/0066731 A1 | 3/2007 | Tattum et al. |
| 2007/0241309 A1 | 10/2007 | Uradnisheck |
| 2008/0161472 A1 | 7/2008 | Jenkins et al. |
| 2008/0255280 A1 | 10/2008 | Sims et al. |
| 2008/0277622 A1 | 11/2008 | Deshpande et al. |
| 2009/0030115 A1 | 1/2009 | Liu |
| 2009/0062297 A1 | 3/2009 | Heidebrecht et al. |
| 2009/0278087 A1 | 11/2009 | Deshpande et al. |
| 2010/0154361 A1 | 6/2010 | Deshpande et al. |
| 2011/0117301 A1 | 5/2011 | Desphande |
| 2011/0171405 A1 | 7/2011 | Deshpande |
| 2011/0172335 A1 | 7/2011 | Desphande |
| 2011/0251395 A1 | 10/2011 | Deshpande et al. |
| 2011/0275750 A1 | 11/2011 | Bene et al. |
| 2012/0175555 A1 | 7/2012 | Menozzi et al. |
| 2012/0199515 A1 | 8/2012 | Peters et al. |
| 2012/0283366 A1 | 11/2012 | Akkapeddi et al. |
| 2013/0158182 A1 | 6/2013 | Menozzi et al. |
| 2013/0285277 A1 | 10/2013 | Behrendt et al. |
| 2016/0052694 A1 | 2/2016 | Li et al. |

FOREIGN PATENT DOCUMENTS

| | | |
|---|---|---|
| AU | 2013256532 | 4/2013 |
| AU | 2015305288 | 8/2015 |
| AU | 2017200768 | 2/2017 |
| BR | 8807141 | 10/1989 |
| BR | 8906385 | 8/1990 |
| BR | 9707824 | 7/1999 |
| CA | 1272341 A1 | 7/1990 |
| CA | 2247985 A1 | 9/1997 |
| CA | 2597918 | 2/2006 |
| CA | 2893166 | 2/2006 |
| CA | 2687081 | 5/2008 |
| CA | 2871480 | 4/2013 |
| CA | 2959027 | 8/2015 |
| CN | 101072820 A | 11/2007 |
| CN | 101193976 A | 6/2008 |
| CN | 101688020 A | 3/2010 |
| CN | 101688020 A | 3/2010 |
| CN | 102199337 A | 9/2011 |
| CN | 104017241 | 9/2014 |
| CN | 104379654 | 2/2015 |
| DE | 442774 C | 4/1927 |
| EP | 0144807 A2 | 6/1985 |
| EP | 0301719 A1 | 2/1989 |
| EP | 0335520 A1 | 10/1989 |
| EP | 0794053 A2 | 9/1997 |
| EP | 1442993 A1 | 8/2004 |
| EP | 1655238 A1 | 5/2006 |
| EP | 1848659 | 10/2007 |
| EP | 2152794 | 2/2010 |
| EP | 2460855 | 6/2012 |
| EP | 2754690 | 7/2014 |
| EP | 2844692 | 3/2015 |
| EP | 3183292 | 6/2017 |
| GB | 1490671 A | 11/1977 |
| HK | 1162562 A | 8/2012 |
| JP | S51-100143 | 9/1976 |
| JP | H01-026667 A | 1/1989 |
| JP | 1993-140555 | 8/1993 |
| JP | 1994-306360 | 1/1994 |
| JP | 2007-556245 | 2/2006 |
| JP | 2017-101689 | 5/2008 |
| JP | 2010-527389 | 8/2010 |
| JP | 2013-086037 | 4/2013 |
| JP | 2015-510375 | 4/2013 |
| JP | 2013-216896 | 10/2013 |
| JP | 2015-249201 | 12/2015 |
| KR | 20147033569 | 4/2013 |
| KR | 10-1537826 | 7/2015 |
| RU | 2007134372 | 2/2006 |
| RU | 2307846 C2 | 10/2007 |
| RU | 2406741 C2 | 12/2010 |
| RU | 2009145713 | 6/2011 |
| RU | 2009145713 A | 6/2011 |
| RU | 2014148149 | 4/2013 |
| RU | 2013142425 | 4/2015 |
| TW | 200904872 | 2/2009 |
| TW | 201439163 | 10/2014 |
| WO | WO-1989/001012 A1 | 2/1989 |
| WO | WO-1995/02616 A2 | 1/1995 |
| WO | WO-2004/063247 A1 | 7/2004 |
| WO | WO-2005/023530 A1 | 3/2005 |
| WO | WO-2006/062816 A2 | 6/2006 |
| WO | WO-2006/088889 A2 | 8/2006 |
| WO | WO 2006/088889 A2 | 8/2006 |
| WO | WO-2008/141185 A1 | 11/2008 |
| WO | WO 2008/141185 A1 | 11/2008 |
| WO | WO-2009/152114 A1 | 12/2009 |
| WO | WO-2012/000614 A1 | 1/2012 |
| WO | WO2013/165971 | 11/2013 |
| WO | WO-2013/165971 A1 | 11/2013 |
| WO | WO 2016/029120 | 2/2016 |
| WO | WO 2016/061503 | 4/2016 |

OTHER PUBLICATIONS

De Almeida, M. V. et al. (2007) "Thalidomide Analogs from Diamines: Synthesis and Evaluation as Inhibitors of TNF-[alpha] Production," Chemical & Pharmaceutical Bulletin, 55(2): 223-226.

Devlieghere, F. et al. (2004) *International Dairy Journal*, 14: 273-285.

Grawe, T. et al. (2002) "Self-Assembly of Ball-Shaped Molecular Complexes in Water," *Journal of Organic Chemistry*, 67(11): 3755-3763.

Hara, S. et al. (1975) "Allylic Polymers, 1: Synthesis of Polyallyl Compounds Containing 4-Oxycarbonylphthalimido Units and Their Polymers," *Die Makromolekulare Chemie* 176(1): 127-141. (English Abstract).

Keenan, R. M. et al. (1999) "Conformational Preferences in a Benzodiazepine Series of Potent Nonpeptide Fibrinogen Receptor Antagonists," *Journal of Medicinal Chemistry*, 42(4): 545-559.

Knollmuller, M. (1974) *Monatshefte Fur Chemie*, 105: 114-122. (English Abstract).

Kricheldorf, H. R. (1980) "15N NMR Spectroscopy: 28-Solvent Effects on the 15N-13C Coupling Constants of Amides, Imides, Ureas, and Polypeptides," *OMR Organic Magnetic Resonance*, Heyden & Son Ltd., GB, 14(6): 455-561.

Michaeli, W. (1995) "Plastics Processing: An Introduction," Carl Hanser Verlag, Munich.

"Polymer Mixing: Technology and Engineering," J. L. White, A. Y. Coran, and A. Moet, Eds., Carl Hanser Verlag, Munich, 2001.

"Plastics Compounding: Equipment and Processing," D.B. Todd, Ed., Carl Hanser Verlag, Munich, 1998.

PubChem Database Compound [Online citation] NCBI; Sep. 7, 2005 (Sep. 7, 2005), Database accession No. CID 3317391, pp. 1.

Ragusa, A. et al. (2005) "Novel Enantioselective Receptors for N-Protected; Glutamate and Aspartate," *Chemistry—A European Journal*, 11(19): 5674-5688.

Rosevear, J., et al. (1990) "A Comparison of the Reactions of Some Ethyl N-Arylcarbamates with Those of the Corresponding Acetanilides. II Amidomethylation with N-Hydroxymethylphthalimide," *Austr. J. Chem.*, 43(2): 339-353.

Rossi, S. et al. (2002) "A Highly Enantioselective Receptor for N-Protected Glutamate and Anomalous Solvent-Dependent Binding Properties", *Angew. Chem. Int. Ed.* 41(22): 4233-4236.

Vacca, A. et al. (2004) "A New Tripodal Receptor for Molecular Recognition of Monosaccharides. A Paradigm for Assessing Glycoside Binding Affinities and Selectivities by 1H NMR Spectroscopy," *Journal of the American Chemical Society*, 126(50): 16456-16465.

Yoshito, T. et al. (1998) "Novel Self-Assembly of m-Xylylene Type Dithioureas by Head-to-Tail Hydrogen Bonding," *J. Org. Chem.*, 63: 7481-7489.

(56) References Cited

OTHER PUBLICATIONS

Zhan-Ting, L. et al. (1992) "The Synthesis of Fluorine-Containing Azamacrocyclic Compounds," *Heterocycles* 34(9): 1729-1736.
Response to Office Action filed on Dec. 21, 2011 for CN Pat. App. No. 200880023116.X, which is national phase of Intl. App. No. PCT/US2008/063250, filed May 9, 2008 (Inventor—G. Deshpande et al.; Applicant—Constar International, Inc.; pp. 1-37).
Extended European Search Report dated Jun. 17, 2014 for EP Pat. App. No. 14150235.1, filed Jan. 6, 2014 (Inventor—G. Deshpande et al.; Applicant—Constar International, Inc.; pp. 1-9).
International Search Report with Written Opinion dated Oct. 29, 2008 for Intl. App. No. PCT/US2008/063250, filed May 9, 2008 (Inventor—G. Deshpande et al.; Applicant—Constar International, Inc.; pp. 1-14).
International Preliminary Report on Patentability dated Nov. 10, 2009 for Intl. App. No. PCT/US2008/063250, filed May 9, 2008 (Inventor—G. Deshpande et al.; Applicant—Constar International, Inc.; pp. 1-7).
Search Report dated Mar. 17, 2015 for ROC Pat. App. No. 103123705, divisional of ROC Pat. App. No. 097117502, which is a national phase of Intl. App. No. PCT/US2008/063250, filed May 9, 2008 (Inventor—G. Deshpande et al.; Applicant—Constar International, Inc.; pp. 1-1).
Extended European Search Report dated Jul. 30, 2013 for EP Pat. App. No. 10822439.5, national phase of Intl. App. No. PCT/US2010/050719, Sep. 29, 2010 (Inventor—G. Deshpande; Applicant—Constar International, Inc.; pp. 1-6).
International Search Report with Written Opinion dated Jun. 27, 2011 for Intl. App. No. PCT/US2010/050719, Sep. 29, 2010 (Inventor—G. Deshpande; Applicant—Constar International, Inc.; pp. 1-7).
International Preliminary Report on Patentability dated Apr. 12, 2012 for Intl. App. No. PCT/US2010/050719, Sep. 29, 2010 (Inventor—G. Deshpande; Applicant—Constar International, Inc.; pp. 1-4).
International Search Report with Written Opinion dated Jul. 28, 2011 for Intl. App. No. PCT/US2010/056594, Nov. 12, 2010 (Inventor—G. Deshpande; Applicant—Constar International, Inc.; pp. 1-8).
International Preliminary Report on Patentability dated May 24, 2012 for Intl. App. No. PCT/US2010/056594, Nov. 12, 2010 (Inventor—G. Deshpande; Applicant—Constar International, Inc.; pp. 1-5).
International Preliminary Report on Patentability dated May 15, 2012 for Intl. App. No. PCT/US2010/056598, Nov. 12, 2010 (Inventor—G. Deshpande; Applicant—Constar International, Inc.; pp. 1-7).
International Search Report with Written Opinion dated Aug. 2, 2011 for Intl. App. No. PCT/US2010/056598, Nov. 12, 2010 (Inventor—G. Deshpande; Applicant—Constar International, Inc.; pp. 1-13).
Extended European Search Report dated Mar. 9, 2013 for EP Pat. App. No. 10830816.4, national phase of Intl. App. No. PCT/US2010/056585, Nov. 12, 2010 (Inventor—G. Deshpande; Applicant—Constar International, Inc.; pp. 1-7).
International Preliminary Report on Patentability dated May 24, 2012 for Intl. App. No. PCT/US2010/056585, Nov. 12, 2010 (Inventor—G. Deshpande; Applicant—Constar International, Inc.; pp. 1-6).
International Search Report with Written Opinion dated Jul. 25, 2011 for Intl. App. No. PCT/US2010/056585, Nov. 12, 2010 (Inventor—G. Deshpande; Applicant—Constar International, Inc.; pp. 1-8).
International Search Report and Written Opinion dated Sep. 5, 2013 for Intl. App. No. PCT/US2013/38801, filed Apr. 30, 2013 (Applicant—Constar International LLC // pp. 1-8).
International Preliminary Report on Patentability dated Nov. 4, 2014 for Intl. App. No. PCT/US2013/38801, filed Apr. 30, 2013 (Applicant—Constar International LLC // pp. 1-8).
Supplementary European Search Report dated Jun. 18, 2009 for European Patent No. 06735060.3, National Phase of Intl. App. No. PCT/US2006/005216, Feb. 15, 2005 (Applicant—Constar International, Inc.; pp. 1-5).
European Search Opinion dated Jul. 9, 2009 for European Patent No. 06735060.3, National Phase of Intl. App. No. PCT/US2006/005216, Feb. 15, 2005 (Applicant—Constar International, Inc.; pp. 1-4).
Extended European Search Report dated Jul. 13, 2012 for European Patent No. 11185342.0, Divisional Application of 06735060.3 (Applicant—Constar International, Inc.; pp. 1-25).
International Search Report and Written Opinion dated Nov. 15, 2007 for Intl. App. No. PCT/US2006/05216, filed on Feb. 15, 2006 (Applicant—Constar International, Inc.; pp. 1-12).
International Preliminary Report on Patentability dated Nov. 23, 2007 for Intl. App. No. PCT/US2006/05216, filed on Feb. 15, 2006 (Applicant—Constar International, Inc.; pp. 1-7).
International Search Report and Written Opinion dated Nov. 27, 2015 for application PCT/US15/46307, filed on Aug. 21, 2015 (Applicant—Plastipak Packaging, Inc.) (12 pages).
International Preliminary Report on Patentability dated Feb. 28, 2017 by the International Searching Authority for Patent Application No. PCT/US2015/046307, which was filed on Aug. 21, 2015 and published as WO 2016/029120 on Feb. 25, 2016 (Inventor—Li et al.; Applicant—Plastipak Packaging, Inc.) (7 pages).
International Search Report and Written Opinion dated Mar. 16, 2016 by the International Searching Authority for Patent Application No. PCT/US2015/056016, which was filed on Oct. 16, 2015 and published as WO 2016/061503 on Apr. 21, 2016 (Inventor—Li et al.; Applicant; Plastipak Packaging, Inc.) (12 pages).
International Preliminary Report on Patentability dated Apr. 18, 2017 by the International Searching Authority for Patent Application No. PCT/US2015/056016, which was filed on Oct. 16, 2015 and published as WO 2016/061503 on Apr. 21, 2016 (Inventor—Li et al.; Applicant; Plastipak Packaging, Inc.) (9 pages).
U.S. Appl. No. 12/117,849 (US-2008-0277622 A1/U.S. Pat. No. 7,994,245), filed May 9, 2008 (Nov. 13, 2008; Aug. 9, 2011), Girish Nilkanth Deshpande (Plastipak Packaging, Inc.).
U.S. Appl. No. 13/164,477 (US-2011-0251395-A1/U.S. Pat. No. 8,431,721), filed Jun. 20, 2011 (Oct. 13, 2011; Apr. 30, 2013), Girish Nilkanth Deshpande (Plastipak Packaging, Inc.).
U.S. Appl. No. 13/849,797 (US-2014-0027339-A1/U.S. Pat. No. 9,475,630), filed Mar. 25, 2013 (Jan. 30, 2014; Oct. 25, 2016), Girish Nilkanth Deshpande (Plastipak Packaging, Inc.).
U.S. Appl. No. 15/147,532 (US-2017-0088332-A1/U.S. Pat. No. 10,125,096), filed May 5, 2016 (Mar. 30, 2017; Nov. 13, 2018), Girish Nilkanth Deshpande (Plastipak Packaging, Inc.).
U.S. Appl. No. 16/189,363 (US-2019-0315685-A1/U.S. Pat. No. 10,906,870), filed Nov. 13, 2018 (Oct. 17, 2019; Feb. 2, 2021), Girish Nilkanth Deshpande (Plastipak Packaging, Inc.).
U.S. Appl. No. 17/164,148 20210403423, filed Feb. 1, 2021, Girish Nilkanth Deshpande (Plastipak Packaging, Inc.).
U.S. Appl. No. 13/873,918 (US-2013-0285277-A1), filed Apr. 30, 2013 (Oct. 31, 2013), Kirk Behrendt (Plastipak Packaging, Inc.).
U.S. Appl. No. 14/466,608 (US-2014-0361218-A1), filed Aug. 22, 2014 (Dec. 11, 2014), Kirk Behrendt (Plastipak Packaging, Inc.).
U.S. Appl. No. 11/354,661 (US-2006-0180790-A1/U.S. Pat. No. 7,691,290), filed Feb. 15, 2006 (Aug. 17, 2006; Apr. 6, 2010), Girish Nilkanth Deshpande (Plastipak Packaging, Inc.).
U.S. Appl. No. 11/816,203 (US-2009-0278087-A1), filed Feb. 15, 2006 (Nov. 12, 2009), Girish Nilkanth Deshpande (Plastipak Packaging, Inc.).
U.S. Appl. No. 12/720,049 (US-2010-0154361-A1/U.S. Pat. No. 8,721,920), filed Mar. 9, 2010 (Jun. 24, 2010; May 13, 2014), Girish Nilkanth Deshpande (Plastipak Packaging, Inc.).
U.S. Appl. No. 14/466,717 (US-2016-0052694-A1), filed Aug. 22, 2014 (Feb. 25, 2016), Shenshen Li (Plastipak Packaging, Inc.).
U.S. Appl. No. 16/694,798 (US-2020-0165051-A1), filed Nov. 25, 2019 (May 28, 2020), Shenshen Li (Plastipak Packaging, Inc.).
U.S. Appl. No. 14/517,643 (US-2016-0108207A1/U.S. Pat. No. 10,351,692), filed Oct. 17, 2014 (Apr. 21, 2016, Jul. 16, 2019), Shenshen Li (Plastipak Packaging, Inc.).

(56) References Cited

OTHER PUBLICATIONS

U.S. Appl. No. 16/508,282 (US-2020-0172702A1/U.S. Pat. No. 11,066,536), filed Jul. 10, 2019 (Jun. 4, 2020, Jul. 20, 2021), Shenshen Li (Plastipak Packaging, Inc.).

OXYGEN SCAVENGERS, COMPOSITIONS COMPRISING THE SCAVENGERS, AND ARTICLES MADE FROM THE COMPOSITIONS

CROSS REFERENCE TO RELATED APPLICATION

This application is a continuation of U.S. application Ser. No. 16/508,282, filed on Jul. 10, 2019, which is a continuation of U.S. application Ser. No. 14/517,643, filed on Oct. 17, 2014, now U.S. Pat. No. 10,351,692, the contents of which are hereby incorporated by reference herein in their entireties.

BACKGROUND

Many polymers used in packaging materials and other articles are permeable to oxygen. When oxygen permeates a polymeric composition or article, it can cause oxidative damage to the contents of the package. It is therefore desirable for certain polymer compositions and articles to have oxygen scavenging capability, such that when oxygen permeates the composition or article, oxidative damage can be mitigated.

It is known in the art to include an oxygen scavenger in the packaging structure for the protection of oxygen sensitive materials. Such scavengers are believed to react with oxygen that is trapped in the package or that permeates from outside of the package, thus extending to life of package contents. These packages include films, bottles, containers, and the like. Food, beverages (such as beer and fruit juices), cosmetics, medicines, and the like are particularly sensitive to oxygen exposure and require high barrier properties to oxygen to preserve the freshness of the package contents and avoid changes in flavor, texture and color.

Therefore, a need exists for compounds and compositions having improved oxygen scavenging capacity. These needs and other needs are satisfied by the present invention.

SUMMARY

In accordance with the purpose(s) of the invention, as embodied and broadly described herein, the invention, in one aspect, relates to oxygen scavenger molecules and compounds, compositions comprising the molecules and compounds, and articles prepared from the compositions.

Also disclosed are polymer compositions comprising the disclosed oxygen scavenging molecules.

Also disclosed are articles prepared from the disclosed compounds and compositions.

Also disclosed are methods of making oxygen scavenging molecules and polymer compositions comprising the disclosed oxygen scavenging molecules.

Also disclosed are methods for making articles comprising the disclosed compounds and compositions.

Also disclosed are methods for packaging an oxygen sensitive material using the disclosed compounds and compositions.

Also disclosed are the products and articles of the disclosed methods.

Additional advantages of the invention will be set forth in part in the description which follows, and in part will be obvious from the description, or can be learned by practice of the invention. The advantages of the invention will be realized and attained by means of the elements and combinations particularly pointed out in the appended claims. It is to be understood that both the foregoing general description and the following detailed description are exemplary and explanatory only and are not restrictive of the invention, as claimed.

DETAILED DESCRIPTION

Figure 1:
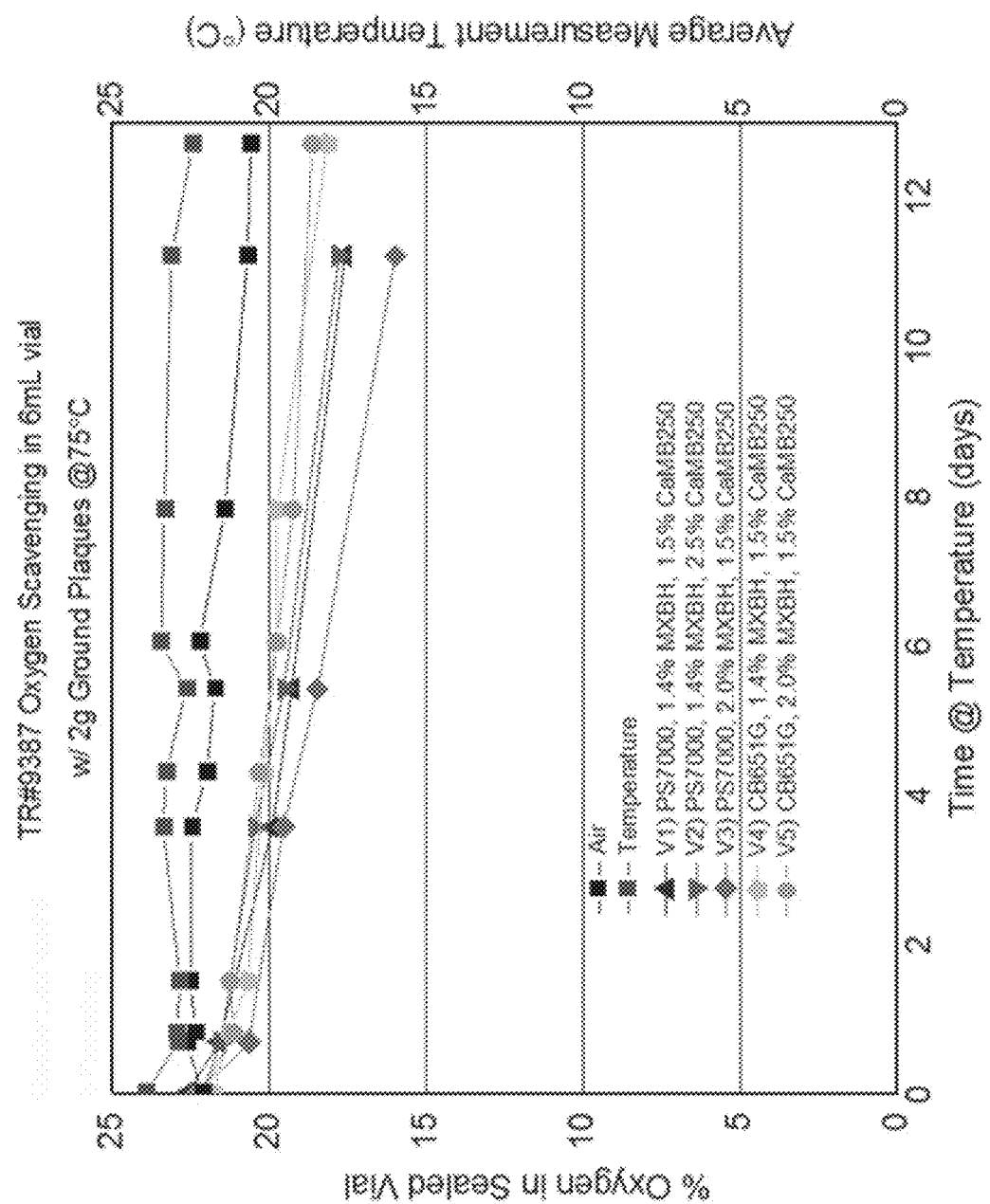
FIG. 1 shows a graph depicting oxygen scavenging data for plaques comprising a representative oxygen scavenger according to the present invention.

The present invention can be understood more readily by reference to the following detailed description of the invention and the Examples included therein.

Before the present compounds, compositions, articles, systems, devices, and/or methods are disclosed and described, it is to be understood that they are not limited to specific synthetic methods unless otherwise specified, or to particular reagents unless otherwise specified, as such may, of course, vary. It is also to be understood that the terminology used herein is for the purpose of describing particular aspects only and is not intended to be limiting. Although any methods and materials similar or equivalent to those described herein can be used in the practice or testing of the present invention, example methods and materials are now described.

Disclosed are the components to be used to prepare the compositions of the invention as well as the compositions themselves to be used within the methods disclosed herein. These and other materials are disclosed herein, and it is understood that when combinations, subsets, interactions, groups, etc. of these materials are disclosed that while specific reference of each various individual and collective combinations and permutation of these compounds cannot be explicitly disclosed, each is specifically contemplated and described herein. For example, if a particular compound is disclosed and discussed and a number of modifications that can be made to a number of molecules including the compounds are discussed, specifically contemplated is each and every combination and permutation of the compound and the modifications that are possible unless specifically indicated to the contrary. Thus, if a class of molecules A, B, and C are disclosed as well as a class of molecules D, E, and F and an example of a combination molecule, A-D is disclosed, then even if each is not individually recited each is individually and collectively contemplated meaning combinations, A-E, A-F, B-D, B-E, B-F, C-D, C-E, and C-F are considered disclosed. Likewise, any subset or combination of these is also disclosed. Thus, for example, the sub-group of A-E, B-F, and C-E would be considered disclosed. This concept applies to all aspects of this application including steps in methods of making and using the compositions of the invention. Thus, if there are a variety of additional steps that can be performed it is understood that each of these additional steps can be performed with any specific embodiment or combination of embodiments of the methods of the invention.

While aspects of the present invention can be described and claimed in a particular statutory class, such as the system statutory class, this is for convenience only and one of skill in the art will understand that each aspect of the present invention can be described and claimed in any statutory class. Unless otherwise expressly stated, it is in no way intended that any method or aspect set forth herein be construed as requiring that its steps be performed in a specific order. Accordingly, where a method claim does not specifically state in the claims or descriptions that the steps are to be limited to a specific order, it is no way intended that an order be inferred, in any respect. This holds for any possible non-express basis for interpretation, including matters of logic with respect to arrangement of steps or operational flow, plain meaning derived from grammatical organization or punctuation, or the number or type of aspects described in the specification.

Throughout this application, various publications are referenced. The disclosures of these publications in their entireties are hereby incorporated by reference into this application in order to more fully describe the state of the art to which this pertains. The references disclosed are also individually and specifically incorporated by reference herein for the material contained in them that is discussed in the sentence in which the reference is relied upon. Nothing herein is to be construed as an admission that the present invention is not entitled to antedate such publication by virtue of prior invention. Further, the dates of publication provided herein may be different from the actual publication dates, which can require independent confirmation.

A. Definitions

In this specification and in the claims that follow, reference will be made to a number of terms, which shall be defined to have the following meanings:

All percentages, ratios and proportions herein are by weight, unless otherwise specified. All temperatures are in degrees Celsius (° C.) unless otherwise specified.

Throughout the description and claims of this specification the word "comprise" and other forms of the word, such as "comprising" and "comprises," means including but not limited to, and is not intended to exclude, for example, other additives, components, integers, or steps.

As used in the specification and the appended claims, the singular forms "a," "an" and "the" include plural referents unless the context clearly dictates otherwise. Thus, for example, reference to "a functional group," "an alkyl," or "a residue" includes mixtures of two or more such functional groups, alkyls, or residues, and the like.

Ranges can be expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that each unit between two particular units are also disclosed. For example, if 10 and 15 are disclosed, then 11, 12, 13, and 14 are also disclosed.

As used herein, the terms "optional" or "optionally" means that the subsequently described event or circumstance may or may not occur, and that the description includes instances where said event or circumstance occurs and instances where it does not.

As used herein, the term "substantially" means that the subsequently described event or circumstance completely occurs or that the subsequently described event or circumstance generally, typically, or approximately occurs. For example, when the specification discloses that substantially all of an agent is released, a person skilled in the relevant art would readily understand that the agent need not be completely released. Rather, this term conveys to a person skilled in the relevant art that the agent need only be released to an extent that an effective amount is no longer unreleased.

As used herein, the term "polymer" refers to a relatively high molecular weight organic compound, natural or synthetic, whose structure can be represented by a repeated small unit, the monomer (e.g., polyethylene, rubber, cellulose). Synthetic polymers are typically formed by addition or condensation polymerization of monomers.

As used herein, the term "copolymer" refers to a polymer formed from two or more different repeating units (monomer residues). By way of example and without limitation, a copolymer can be an alternating copolymer, a random copolymer, a block copolymer, or a graft copolymer. It is also contemplated that, in certain aspects, various block segments of a block copolymer can themselves comprise copolymers.

As used herein, the term "oligomer" refers to a relatively low molecular weight polymer in which the number of repeating units is between two and ten, for example, from two to eight, from two to six, or from two to four. In one aspect, a collection of oligomers can have an average number of repeating units of from about two to about ten, for example, from about two to about eight, from about two to about six, or from about two to about four.

As used herein, the term "molecular weight" (MW) refers to the mass of one molecule of that substance, relative to the unified atomic mass unit u (equal to $1/12$ the mass of one atom of carbon-12).

As used herein, the term "number average molecular weight" ($M_n$) refers to the common, mean, average of the molecular weights of the individual polymers. $M_n$ can be determined by measuring the molecular weight of n polymer molecules, summing the weights, and dividing by n. $M_n$ is calculated by:

$$\overline{M}_n = \frac{\sum_i N_i M_i}{\sum_i N_i},$$

wherein $N_i$ is the number of molecules of molecular weight $M_i$. The number average molecular weight of a polymer can be determined by gel permeation chromatography, viscometry (Mark-Houwink equation), light scattering, analytical ultracentrifugation, vapor pressure osmometry, end-group titration, and colligative properties.

As used herein, the term "weight average molecular weight" ($M_w$) refers to an alternative measure of the molecular weight of a polymer. $M_w$ is calculated by:

$$\overline{M}_w = \frac{\sum_i N_i M_i^2}{\sum_i N_i M_i},$$

wherein $N_i$ is the number of molecules of molecular weight $M_i$. Intuitively, if the weight average molecular weight is w, and a random monomer is selected, then the polymer it belongs to will have a weight of w on average. The weight average molecular weight can be determined by light scattering, small angle neutron scattering (SANS), X-ray scattering, and sedimentation velocity.

As used herein, the terms "polydispersity" and "polydispersity index" (PDI) refer to the ratio of the weight average to the number average ($M_w/M_n$).

As used herein, the term "compatibilizing agent" refers to a small molecule or polymer that has both polar and non-polar functional groups. For example, a fatty-acid ester has both polar and non-polar functional groups.

A weight percent (wt. %) of a component, unless specifically stated to the contrary, is based on the total weight of the formulation or composition in which the component is included.

As used herein, nomenclature for compounds, including organic compounds, can be given using common names, IUPAC, IUBMB, or CAS recommendations for nomenclature. When one or more stereochemical features are present, Cahn-Ingold-Prelog rules for stereochemistry can be employed to designate stereochemical priority, E/Z specification, and the like. One of skill in the art can readily ascertain the structure of a compound if given a name, either by systemic reduction of the compound structure using naming conventions, or by commercially available software, such as CHEMDRAW™ (Cambridgesoft Corporation, U.S.A.).

A residue of a chemical species, as used in the specification and concluding claims, refers to the moiety that is the resulting product of the chemical species in a particular reaction scheme or subsequent formulation or chemical product, regardless of whether the moiety is actually obtained from the chemical species. Thus, an ethylene glycol residue in a polyester refers to one or more —OCH$_2$CH$_2$O— units in the polyester, regardless of whether ethylene glycol was used to prepare the polyester. Similarly, a sebacic acid residue in a polyester refers to one or more —CO(CH$_2$)$_8$CO— moieties in the polyester, regardless of whether the residue is obtained by reacting sebacic acid or an ester thereof to obtain the polyester.

A very close synonym of the term "residue" is the term "radical," which as used in the specification and concluding claims, refers to a fragment, group, or substructure of a molecule described herein, regardless of how the molecule is prepared. For example, a 2,4-thiazolidinedione radical in a particular compound has the structure

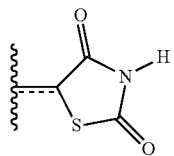

regardless of whether thiazolidinedione is used to prepare the compound. In some embodiments the radical (for example an alkyl) can be further modified (i.e., substituted alkyl) by having bonded thereto one or more "substituent radicals." The number of atoms in a given radical is not critical to the present invention unless it is indicated to the contrary elsewhere herein.

In some aspects, a structure of a compound can be represented by a formula:

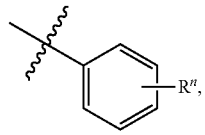

which is understood to be equivalent to a formula:

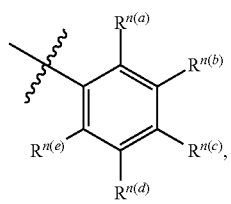

wherein n is typically an integer. That is, $R^n$ is understood to represent five independent substituents, $R^{n(a)}$, $R^{n(b)}$, $R^{n(c)}$, $R^{n(d)}$, $R^{n(e)}$. By "independent substituents," it is meant that each R substituent can be independently defined. For example, if in one instance $R^{n(a)}$ is halogen, then $R^{n(b)}$ is not necessarily halogen in that instance.

As used herein, the term "substituted" is contemplated to include all permissible substituents of organic compounds. In a broad aspect, the permissible substituents include acyclic and cyclic, branched and unbranched, carbocyclic and heterocyclic, and aromatic and nonaromatic substituents of organic compounds. Illustrative substituents include, for example, those described below. The permissible substituents can be one or more and the same or different for appropriate organic compounds. For purposes of this disclosure, the heteroatoms, such as nitrogen, can have hydrogen substituents and/or any permissible substituents of organic compounds described herein which satisfy the valences of the heteroatoms. This disclosure is not intended to be limited in any manner by the permissible substituents of organic compounds. Also, the terms "substitution" or "substituted with" include the implicit proviso that such substitution is in accordance with permitted valence of the substituted atom and the substituent, and that the substitution results in a stable compound, e.g., a compound that does not spontaneously undergo transformation such as by rearrangement, cyclization, elimination, etc.

In defining various terms, "$A^1$," "$A^2$," "$A^3$," and "$A^4$" are used herein as generic symbols to represent various specific substituents. These symbols can be any substituent, not limited to those disclosed herein, and when they are defined to be certain substituents in one instance, they can, in another instance, be defined as some other substituents.

The term "alkyl" as used herein is a branched or unbranched saturated hydrocarbon group of from 1 to 24 carbon atoms, for example from 1 to 12 carbons, from 1 to 8 carbons, from 1 to 6 carbons, or from 1 to 4 carbons, such as methyl, ethyl, n-propyl, isopropyl, n-butyl, isobutyl, s-butyl, t-butyl, n-pentyl, isopentyl, s-pentyl, neopentyl, hexyl, heptyl, octyl, nonyl, decyl, dodecyl, tetradecyl, hexadecyl, eicosyl, tetracosyl, and the like. The alkyl group can be cyclic or acyclic. The alkyl group can be branched or unbranched. The alkyl group can also be substituted or unsubstituted. For example, the alkyl group can be substituted with one or more groups including optionally substituted alkyl, cycloalkyl, alkoxy, amino, ether, halide, hydroxy, nitro, silyl, sulfo-oxo, or thiol, as described herein. A "lower alkyl" group is an alkyl group containing from one to six (e.g., from one to four) carbon atoms.

Throughout the specification "alkyl" is generally used to refer to both unsubstituted alkyl groups and substituted alkyl groups; however, substituted alkyl groups are also specifically referred to herein by identifying the specific substituent(s) on the alkyl group. For example, the term "halogenated alkyl" specifically refers to an alkyl group that is substituted with one or more halide, e.g., fluorine, chlorine, bromine, or iodine. The term "alkoxyalkyl" specifically refers to an alkyl group that is substituted with one or more alkoxy groups, as described below. The term "alkylamino" specifically refers to an alkyl group that is substituted with one or more amino groups, as described below, and the like. When "alkyl" is used in one instance and a specific term such as "alkylalcohol" is used in another, it is not meant to imply that the term "alkyl" does not also refer to specific terms such as "alkylalcohol" and the like.

This practice is also used for other groups described herein. That is, while a term such as "cycloalkyl" refers to both unsubstituted and substituted cycloalkyl moieties, the substituted moieties can, in addition, be specifically identified herein; for example, a particular substituted cycloalkyl can be referred to as, e.g., an "alkylcycloalkyl." Similarly, a substituted alkoxy can be specifically referred to as, e.g., a "halogenated alkoxy," a particular substituted alkenyl can be, e.g., an "alkenylalcohol," and the like. Again, the practice of using a general term, such as "cycloalkyl," and a specific term, such as "alkylcycloalkyl," is not meant to imply that the general term does not also include the specific term.

The term "cycloalkyl" as used herein is a non-aromatic carbon-based ring composed of at least three carbon atoms. Examples of cycloalkyl groups include, but are not limited to, cyclopropyl, cyclobutyl, cyclopentyl, cyclohexyl, norbornyl, and the like. The term "heterocycloalkyl" is a type of cycloalkyl group as defined above, and is included within the meaning of the term "cycloalkyl," where at least one of the carbon atoms of the ring is replaced with a heteroatom such as, but not limited to, nitrogen, oxygen, sulfur, or phosphorus. The cycloalkyl group and heterocycloalkyl group can be substituted or unsubstituted. The cycloalkyl group and heterocycloalkyl group can be substituted with one or more groups including optionally substituted alkyl, cycloalkyl, alkoxy, amino, ether, halide, hydroxy, nitro, silyl, sulfo-oxo, or thiol as described herein.

The terms "alkoxy" and "alkoxyl" as used herein to refer to an alkyl or cycloalkyl group bonded through an ether linkage; that is, an "alkoxy" group can be defined as —OA$^1$ where A$^1$ is alkyl or cycloalkyl as defined above. "Alkoxy" also includes polymers of alkoxy groups as just described; that is, an alkoxy can be a polyether such as —OA$^1$-OA$^2$ or —OA$^1$-(OA$^2$)$_a$-OA$^3$, where "a" is an integer of from 1 to 200 and A$^1$, A$^2$, and A$^3$ are alkyl and/or cycloalkyl groups.

The term "alkenyl" as used herein is a hydrocarbon group of from 2 to 24 carbon atoms with a structural formula containing at least one carbon-carbon double bond. Asymmetric structures such as (A$^1$A$^2$)C=C(A$^3$A$^4$) are intended to include both the E and Z isomers. This can be presumed in structural formulae herein wherein an asymmetric alkene is present, or it can be explicitly indicated by the bond symbol C=C. The alkenyl group can be substituted with one or more groups including optionally substituted alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol, as described herein.

The term "cycloalkenyl" as used herein is a non-aromatic carbon-based ring composed of at least three carbon atoms and containing at least one carbon-carbon double bound, i.e., C=C. Examples of cycloalkenyl groups include, but are not limited to, cyclopropenyl, cyclobutenyl, cyclopentenyl, cyclopentadienyl, cyclohexenyl, cyclohexadienyl, norbornenyl, and the like. The term "heterocycloalkenyl" is a type of cycloalkenyl group as defined above, and is included within the meaning of the term "cycloalkenyl," where at least one of the carbon atoms of the ring is replaced with a heteroatom such as, but not limited to, nitrogen, oxygen, sulfur, or phosphorus. The cycloalkenyl group and heterocycloalkenyl group can be substituted or unsubstituted. The cycloalkenyl group and heterocycloalkenyl group can be substituted with one or more groups including optionally substituted alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol as described herein.

The term "alkynyl" as used herein is a hydrocarbon group of 2 to 24 carbon atoms with a structural formula containing at least one carbon-carbon triple bond. The alkynyl group can be unsubstituted or substituted with one or more groups including optionally substituted alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol, as described herein.

The term "cycloalkynyl" as used herein is a non-aromatic carbon-based ring composed of at least seven carbon atoms and containing at least one carbon-carbon triple bond. Examples of cycloalkynyl groups include, but are not limited to, cycloheptynyl, cyclooctynyl, cyclononynyl, and the like. The term "heterocycloalkynyl" is a type of cycloalkenyl group as defined above, and is included within the meaning of the term "cycloalkynyl," where at least one of the carbon atoms of the ring is replaced with a heteroatom such as, but not limited to, nitrogen, oxygen, sulfur, or phosphorus. The cycloalkynyl group and heterocycloalkynyl group can be substituted or unsubstituted. The cycloalkynyl group and heterocycloalkynyl group can be substituted with one or more groups including optionally substituted alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol, as described herein.

The term "aryl" as used herein is a group that contains any carbon-based aromatic group including benzene, naphthalene, phenyl, biphenyl, phenoxybenzene, and the like. The term "aryl" also includes "heteroaryl," which is defined as a group that contains an aromatic group that has at least one heteroatom incorporated within the ring of the aromatic group. Examples of heteroatoms include, but are not limited to, nitrogen, oxygen, sulfur, and phosphorus. Likewise, the term "non-heteroaryl," which is also included in the term "aryl," defines a group that contains an aromatic group that does not contain a heteroatom. The aryl group can be substituted or unsubstituted. The aryl group can be substituted with one or more groups including optionally substituted alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol as described herein. The term "biaryl" is a specific type of aryl group and is included in the definition of "aryl." Biaryl refers to two aryl groups that are bound together via a fused ring structure, as in naphthalene, or are attached via one or more carbon-carbon bonds, as in biphenyl.

The term "aldehyde" as used herein is represented by the formula —C(O)H. Throughout this specification "C(O)" is a short hand notation for a carbonyl group, i.e., C=O.

The terms "amine" or "amino" as used herein are represented by the formula $NA^1A^2A^3$, where $A^1$, $A^2$, and $A^3$ can be, independently, hydrogen or optionally substituted alkyl, cycloalkyl, alkenyl, cycloalkenyl, alkynyl, cycloalkynyl, aryl, or heteroaryl group as described herein.

The term "carboxylic acid" as used herein is represented by the formula —C(O)OH.

The term "ester" as used herein is represented by the formula —OC(O)$A^1$ or —C(O)O$A^1$, where $A^1$ can be an optionally substituted alkyl, cycloalkyl, alkenyl, cycloalkenyl, alkynyl, cycloalkynyl, aryl, or heteroaryl group as described herein. The term "polyester" as used herein is represented by the formula -($A^1$O(O)C-$A^2$-C(O)O)$_a$— or -($A^1$O(O)C-$A^2$-OC(O))$_a$—, where $A^1$ and $A^2$ can be, independently, an optionally substituted alkyl, cycloalkyl, alkenyl, cycloalkenyl, alkynyl, cycloalkynyl, aryl, or heteroaryl group described herein and "a" is an integer from 1 to 500. "Polyester" is as the term used to describe a group that is produced by the reaction between a compound having at least two carboxylic acid groups with a compound having at least two hydroxyl groups.

The term "ether" as used herein is represented by the formula $A^1OA^2$, where $A^1$ and $A^2$ can be, independently, an optionally substituted alkyl, cycloalkyl, alkenyl, cycloalkenyl, alkynyl, cycloalkynyl, aryl, or heteroaryl group described herein. The term "polyether" as used herein is represented by the formula -($A^1$O-$A^2$O)$_a$—, where $A^1$ and $A^2$ can be, independently, an optionally substituted alkyl, cycloalkyl, alkenyl, cycloalkenyl, alkynyl, cycloalkynyl, aryl, or heteroaryl group described herein and "a" is an integer of from 1 to 500. Examples of polyether groups include polyethylene oxide, polypropylene oxide, and polybutylene oxide.

The term "halide" as used herein refers to the halogens fluorine, chlorine, bromine, and iodine.

The term "heterocycle" as used herein refers to single and multi-cyclic aromatic or non-aromatic ring systems in which at least one of the ring members is other than carbon. Heterocycle includes pyridinde, pyrimidine, furan, thiophene, pyrrole, isoxazole, isothiazole, pyrazole, oxazole, thiazole, imidazole, oxazole, including, 1,2,3-oxadiazole, 1,2,5-oxadiazole and 1,3,4-oxadiazole, thiadiazole, including, 1,2,3-thiadiazole, 1,2,5-thiadiazole, and 1,3,4-thiadiazole, triazole, including, 1,2,3-triazole, 1,3,4-triazole, tetrazole, including 1,2,3,4-tetrazole and 1,2,4,5-tetrazole, pyridine, pyridazine, pyrimidine, pyrazine, triazine, including 1,2,4-triazine and 1,3,5-triazine, tetrazine, including 1,2,4,5-tetrazine, pyrrolidine, piperidine, piperazine, morpholine, azetidine, tetrahydropyran, tetrahydrofuran, dioxane, and the like.

The term "hydroxyl" as used herein is represented by the formula —OH.

The term "ketone" as used herein is represented by the formula $A^1$C(O)$A^2$, where $A^1$ and $A^2$ can be, independently, an optionally substituted alkyl, cycloalkyl, alkenyl, cycloalkenyl, alkynyl, cycloalkynyl, aryl, or heteroaryl group as described herein.

The term "azide" as used herein is represented by the formula —$N_3$.

The term "nitro" as used herein is represented by the formula —$NO_2$.

The term "nitrile" as used herein is represented by the formula —CN.

The term "thiol" as used herein is represented by the formula —SH.

The terms "electron-withdrawing" or "electron-donating" as used herein refer to the ability of a substituent to withdraw or donate electrons relative to that of hydrogen, if hydrogen occupied the same position in the molecule. These terms are well-understood by one skilled in the art and are discussed, for example, in Advanced Organic Chemistry by J. March, 1985, pp. 16-18. Electron withdrawing groups can include fluoro, chloro, bromo, nitro, acyl, cyano, carboxyl, lower alkenyl, lower alkynyl, carboxaldehyde, carboxyamido, aryl, quaternary ammonium, trifluoro-methyl, alkoxycarbonyl, aryloxycarbonyl, aminocarbonyl, sulfonic, alkanesulfonyl, arylsulfonyl, perfluoroalkanesulfonyl, perfluoroarylsulfonyl, phosphoryl, tertiary amine cation and a combination thereof, among others. Electron donating groups can include such groups as hydroxy, lower alkoxy, lower alkyl, amino, lower alkylamino, di(lower alkyl)amino, aryloxy, mercapto, lower alkylthio, lower alkylmercapto and disulfide among others. One skilled in the art will appreciate that the aforesaid substituents may have electron donating or electron withdrawing properties under different chemical conditions.

Certain instances of the above defined terms may occur more than once in the structural formulae, and upon such occurrence each term shall be defined independently of the other.

As used herein, the term "effective amount" refers to an amount that is sufficient to achieve the desired result or to have an effect on an undesired condition. For example, a "visually effective amount" refers to an amount that is sufficient to achieve the desired result (i.e., impart color to a composition or an article), but is generally insufficient to cause adverse side effects (e.g., warping of a polymeric article).

As used herein, the term "leaving group" refers to an atom (or a group of atoms) with electron withdrawing ability that can be displaced as a stable species, taking with it the bonding electrons. Examples of suitable leaving groups include sulfonate esters, including triflate, mesylate, tosylate, brosylate, and halides.

Compounds described herein can contain one or more double bonds and, thus, potentially give rise to cis/trans (E/Z) isomers, as well as other conformational isomers. Unless stated to the contrary, the invention includes all such possible isomers, as well as mixtures of such isomers.

Unless stated to the contrary, a formula with chemical bonds shown only as solid lines and not as wedges or dashed lines contemplates each possible isomer, e.g., each enantiomer and diastereomer, and a mixture of isomers, such as a racemic or scalemic mixture. Compounds described herein can contain one or more asymmetric centers and, thus, potentially give rise to diastereomers and optical isomers. Unless stated to the contrary, the present invention includes all such possible diastereomers as well as their racemic mixtures, their substantially pure resolved enantiomers, all possible geometric isomers, and pharmaceutically acceptable salts thereof. Mixtures of stereoisomers, as well as isolated specific stereoisomers, are also included. During the course of the synthetic procedures used to prepare such compounds, or in using racemization or epimerization procedures known to those skilled in the art, the products of such procedures can be a mixture of stereoisomers.

B. Compounds and Compositions

1. Oxygen Scavengers

In various aspects, the present invention relates to oxygen scavenging compounds. In one aspect, the disclosed oxygen scavenging compounds comprise at least one aryl group attached to a heteroatom. In a further aspect, at least one of the methylene positions of the aryl group has no substitutions. In a still further aspect, the disclosed oxygen scavenging compounds is an amine-based compound. The oxygen scavenging ability of the disclosed compounds can be enhanced, in various aspects, by the presence of a transition metal. In some aspects, the disclosed oxygen scavenging compounds can be polymeric. In other aspects, the oxygen scavenging compounds can be nonpolymeric.

In one aspect, the disclosed oxygen scavenging compounds can have the general structure shown below:

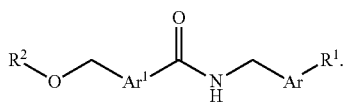
(I)

In a further aspect, each Ar is aryl or heteroaryl; each $Ar^1$ is aryl or heteroaryl; and each $Ar^1$ is substituted with 0, 1, 2, or 3 groups independently selected from halogen, C1-C4 alkyl, electron withdrawing groups, and electron donating groups, and valence is satisfied. In a still further aspect, each $R^1$ represents five groups independently selected from hydrogen, halogen, C1-C4 alkyl,

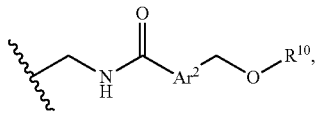

electron withdrawing groups, and electron donating groups.

In a further aspect, each $Ar^2$ is independently aryl or heteroaryl; and each $Ar^2$ is independently substituted with 0, 1, 2, or 3 groups independently selected from halogen, C1-C4 alkyl, electron withdrawing groups and electron donating groups, and valence is satisfied; and each $R^{10}$ is independently selected from hydrogen, C1-C4 alkyl, —C(O)$R^{20}$, and —C(O)$Ar^3$. In a still further aspect, each $R^{20}$ is C1-C4 alkyl; and each $Ar^3$ is phenyl or naphthyl; and each $Ar^3$ is independently substituted with 0, 1, 2, or 3 groups independently selected from halogen, C1-C4 alkyl, —CO$_2R^{30}$; electron withdrawing group and electron donating groups, and valence is satisfied.

In a further aspect, each $R^{30}$ is selected from hydrogen, C1-C4 alkyl, —(CH$_2$)$_n$OH, and —CH$_2Ar^4$; and n is an integer selected from 1 or 2. In a still further aspect, each $Ar^4$ is aryl substituted with 0, 1, 2, and 3 groups selected from halogen, C1-C4 alkyl, and —C(O)NHCH$_2Ar^5$. In a yet further aspect, each $Ar^5$ is aryl substituted with 0, 1, 2, or 3 groups independently selected from halogen, C1-C4 alkyl,

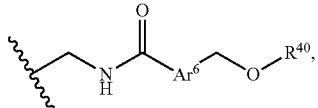

electron withdrawing groups, and electron donating groups. In a yet further aspect, each $R^{40}$ is independently selected from hydrogen, C1-C4 alkyl, electron withdrawing groups, and electron donating groups; and each $Ar^6$ is aryl substituted with 0, 1, 2, and 3 groups independently selected from hydrogen, C1-C4 alkyl, electron withdrawing groups, and electron donating groups;

In a further aspect, each $R^2$ is independently selected from hydrogen, C1-C4 alkyl, —C(O)$R^{50}$, and —C(O)$Ar^7$; each $R^{50}$ is C1-C4 alkyl; each $Ar^7$ is aryl substituted with 0, 1, 2, and 3 groups independently selected from hydrogen, C1-C4 alkyl, and electron withdrawing groups, and electron donating groups, and valence is satisfied.

In a further aspect, Ar is aryl; $Ar^1$ is aryl; and the compound has the structure:

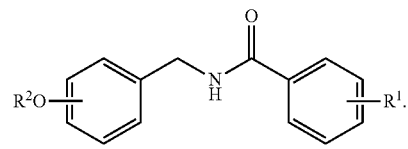

In a further aspect, Ar is aryl; $Ar^1$ is aryl; one of the five groups representing $R^1$ is

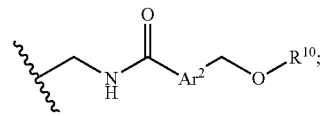

$Ar^2$ is aryl; and the compound has the structure:

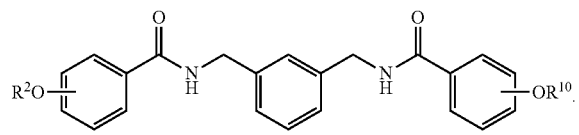

In a further aspect, Ar is aryl; $Ar^1$ is aryl; two of the five groups representing $R^1$ is

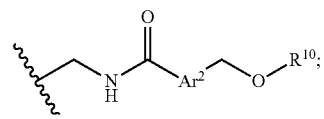

$Ar^2$ is aryl; and the compound has the structure:

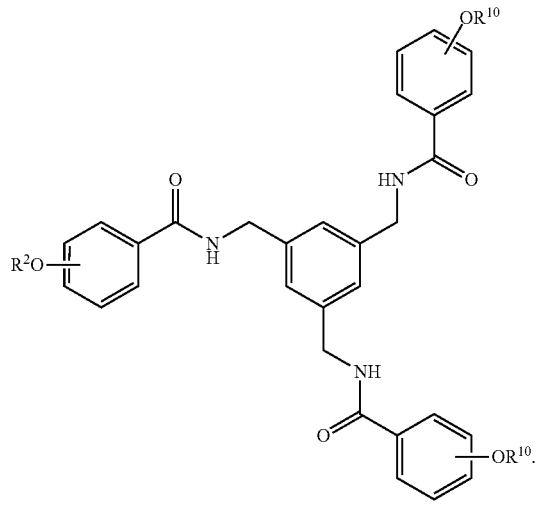

In a further aspect, Ar is aryl; Ar¹ is aryl; one of the five groups representing R¹ is

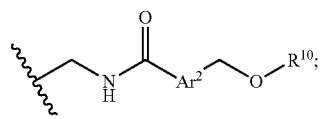

Ar² is aryl; Ar³ is naphthyl; Ar⁴ is phenyl; Ar⁵ is phenyl; and the compound has the structure:

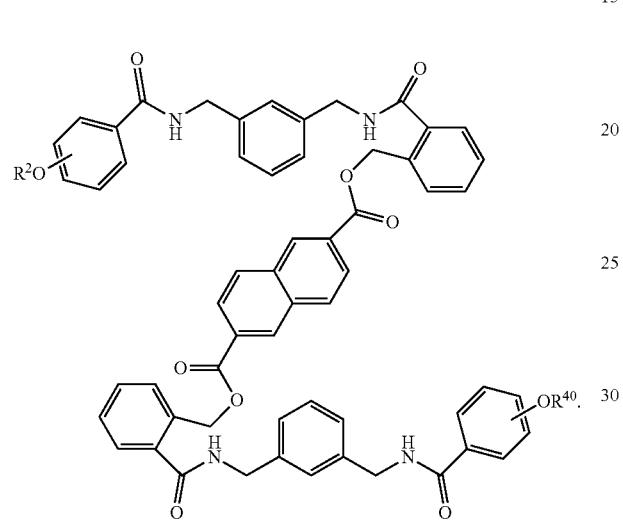

In a further aspect, Ar is monocyclic. In a still further aspect, Ar is para or meta substituted phenyl.

In a further aspect, the compound can have the structure

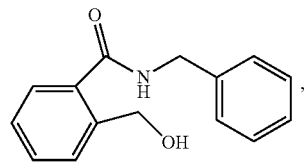

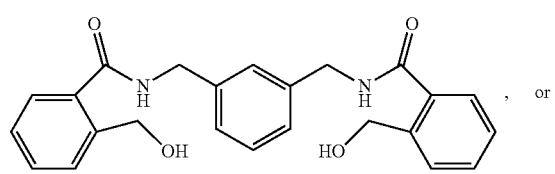, or

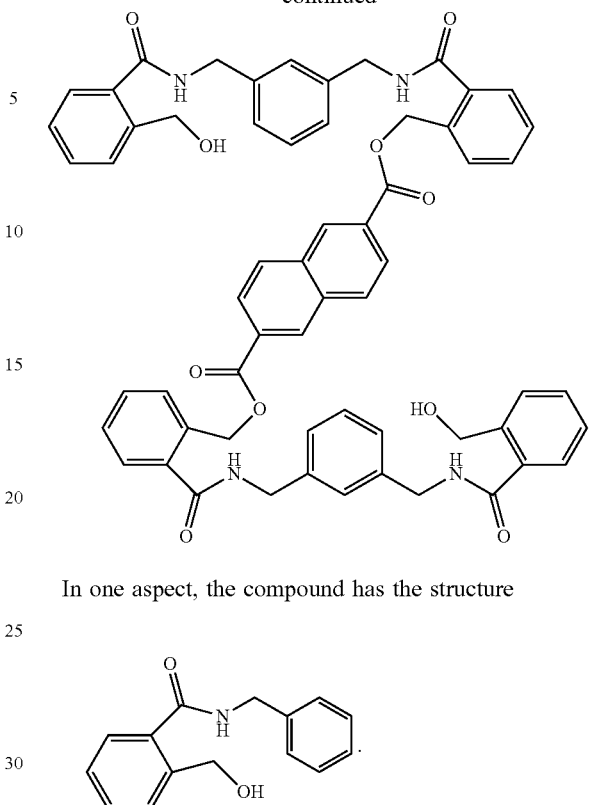

In one aspect, the compound has the structure

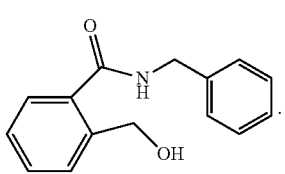 [SMILES: O=C(NCc1ccccc1)c1ccccc1CO]

In another aspect, the compound has the structure

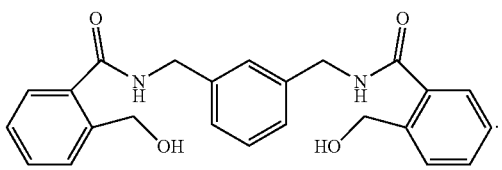 [SMILES: O=C(NCc1cccc(CNC(=O)c2ccccc2CO)c1)c1ccccc1CO]

In another aspect, the compound has the structure

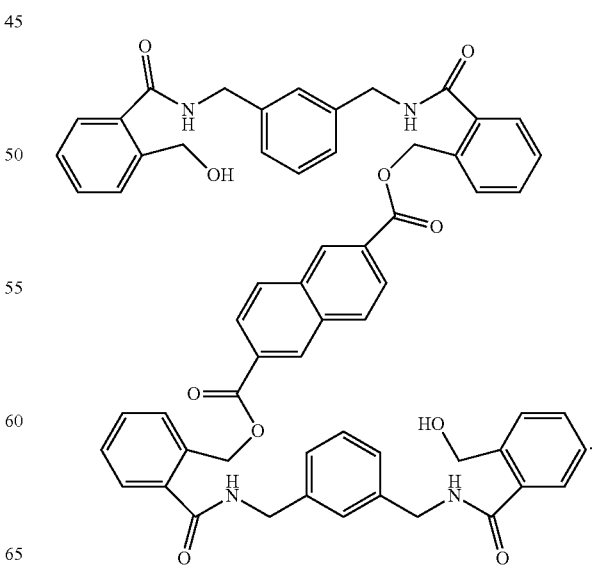

In a further aspect, the oxygen scavenger compound is polymeric or copolymeric. In a still further aspect, the compound is a polymer comprising at least one residue having the formula:

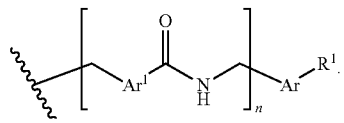
(II)

In a further aspect, each of the at least one residue is covalently bonded as a repeating unit in the polymer chain, covalently bonded as a side-chain pendant group, or covalently bonded as an end group of the polymer. In a still further aspect, n is 2, 3, 4, 5, or 6; each Ar is aryl or heteroaryl; each $Ar^1$ is aryl or heteroaryl; and each $Ar^1$ is substituted with 0, 1, 2, or 3 groups independently selected from halogen, C1-C4 alkyl, electron withdrawing groups, and electron donating groups, and valence is satisfied. In a yet further aspect, each $R^1$ represents 6-n groups independently selected from hydrogen, halogen, C1-C4 alkyl, electron withdrawing groups, and electron donating groups.

In a further aspect, the at least one residue is a repeating unit in the polymer chain. In a still further aspect, the residue comprises:

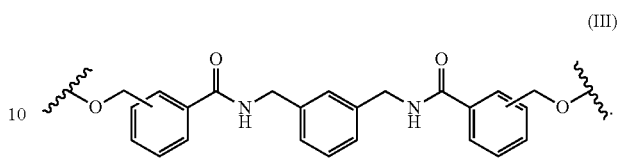
(III)

In another aspect, the residue comprises:

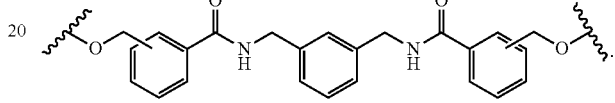
(III)

In a further aspect, the repeating unit comprises:

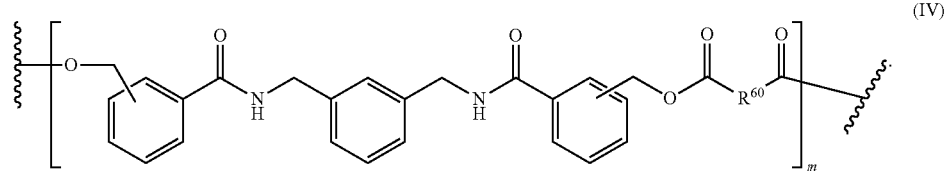
(IV)

In a still further aspect, the repeating unit comprises:

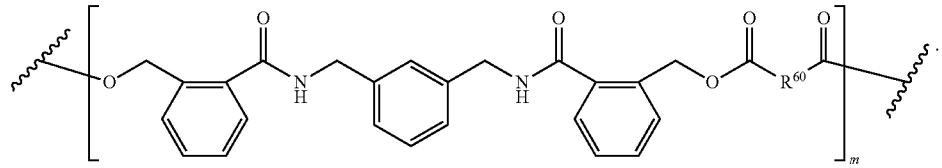

In a yet further aspect, $R^{60}$ is phenyl or $-(CH_2)_o-$; and o is an integer 0 to 10. In a still further aspect, $R^{60}$ is substituted with 0, 1, 2, 3, or 4 groups independently selected from electron withdrawing groups and electron donating groups, and valence is satisfied. In an even further aspect, m is an integer 2 or greater. For example, m can be from 2 to about 10,000, or from 2 to about 1,000, or from 2 to about 100.

In some aspects, the compound has the structure:

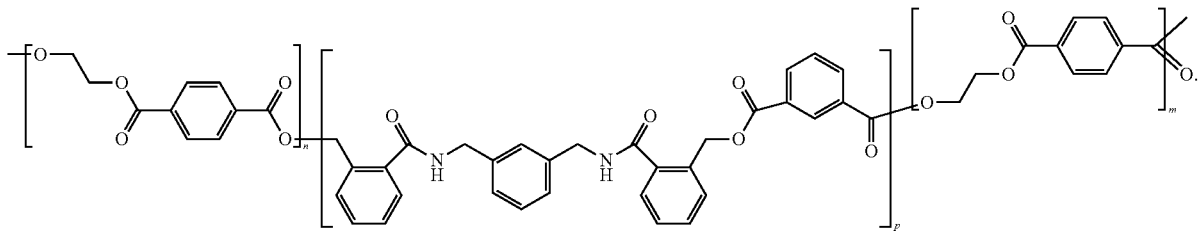

In other aspects, the compound has the structure:

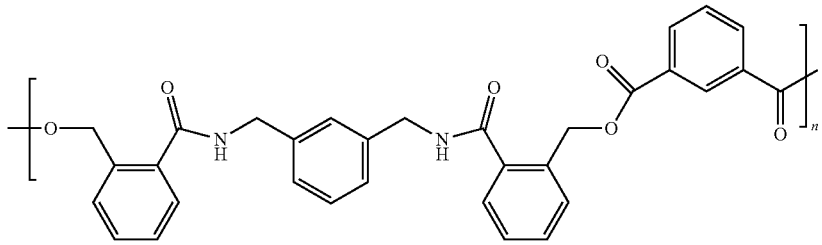

In a further aspect, m is an integer 1 or greater. For example, m can be from 1 to about 10,000, or from 1 to about 1,000, or from 1 to about 100. In a still further aspect, n is an integer 1 or greater. For example, n can be from 1 to about 10,000, or from 1 to about 1,000, or from 1 to about 100. In an even further aspect, 9 is an integer 1 or greater. For example, n can be from 1 to about 1,000, or from 1 to about 100.

In a further aspect, the alkyl group of the disclosed oxygen scavenging compound can be a branched or unbranched saturated hydrocarbon group of 1 to 24 carbon atoms, e.g. 1 to 18 carbons atoms, 1 to 14 carbon atoms, 1 to 12 carbon atoms, 1 to 10 carbon atoms, 1 to 8, 1 to 6 carbon atoms, or 1 to 4 carbon atoms, such as methyl, ethyl, n-propyl, isopropyl, n-butyl, isobutyl, t-butyl, pentyl, hexyl, heptyl, octyl, decyl, tetradecyl, hexadecyl, eicosyl, tetracosyl and the like. The alkyl group can be substituted or unsubstituted. The alkyl group can be substituted with one or more groups including, but not limited to, alkyl, halogenated alkyl, alkoxy, alkenyl, alkynyl, aryl, heteroaryl, aldehyde, amino, carboxylic acid, ester, halide, hydroxamate, hydroxy, ketone, nitro, silyl, sulfo-oxo, sulfonyl, sulfone, sulfoxide, or thiol, as described below. The alkyl group can be halogenated, which includes an alkyl group that is substituted with one or more halide, e.g., fluorine, chlorine, bromine, or iodine. The alkyl group can also be a lower alkyl group, which is an alkyl group containing from one to six (e.g., from one to four) carbon atoms.

In a further aspect, the aryl group of the disclosed oxygen scavenging compound can be any carbon-based aromatic group including but not limited to, benzene, naphthalene, phenyl, biphenyl, etc. The aryl group can also be heteroaryl, which is defined as an aromatic group that has at least one heteroatom incorporated within the ring of the aromatic group. Examples of heteroatoms include, but are not limited to, nitrogen, oxygen, sulfur, and phosphorus. The aryl group can be substituted or unsubstituted. The aryl group can be substituted with one or more groups including, but not limited to, alkyl, halogenated alkyl, alkoxy, alkenyl, alkynyl, aryl, heteroaryl, aldehyde, amino, carboxylic acid, ester, halide, hydroxamate, hydroxy, ketone, nitro, silyl, sulfo-oxo, sulfonyl, sulfone, sulfoxide, or thiol as described herein. A biaryl group is a specific type of aryl group and is included in the definition of aryl. Biaryl refers to two aryl groups that are bound together via a fused ring structure, as in naphthalene, or are attached via one or more carbon-carbon bonds, as in biphenyl.

In a further aspect, suitable electron withdrawing groups and electron releasing or donating groups for use in the present invention are generally known in the art. Exemplary electron withdrawing groups include nitro, carboxylic acid, esters, for example loweralkyl esters, and cyano. Exemplary electron releasing or donating groups include branched and straight chain alkyl groups, for example, methyl, ethyl, propyl, isopropyl, butyl, isobutyl, and tert-butyl. Other exemplary electron releasing groups include alkoxy, for example methoxy and ethoxy. Other exemplary electron releasing groups include thioalkyl. Still other exemplary electron releasing groups include amines, for example —NH$_2$, and NH(loweralkyl), and N(loweralkyl)$_2$.

The oxygen scavenging compound can, in certain aspects be complexed to a transition metal. For example, the oxygen scavenging compound can be complexed to the transition metal through one or more aryl groups, for example through pi-cloud complexation. The oxygen scavenging compound can also be polymerized via complexation to the transition metal.

2. Oxygen Scavenging Compositions

In various aspects, also described herein are compositions comprising the disclosed oxygen scavengers. In one aspect, the disclosed compositions are oxygen scavenging compositions. Generally, the disclosed oxygen scavenging composition comprises a base polymer; an oxygen scavenger compound of Formula (I)-(IV) present in an amount of from about 0.10 to about 10 weight percent of the composition; and optionally, a transition metal in a positive oxidation state, the metal present in an amount of from about 10 ppm to about 400 ppm.

In a further aspect, the oxygen scavenging compositions comprise from about 0.10% to about 10% weight percent of the oxygen scavenger. In one aspect, the compositions comprise from about 0.5% to about 10% by weight of an oxygen scavenger. In still further aspect, the compositions comprise from about 1% to about 5% by weight of an oxygen scavenger. In a yet further aspect, the compositions comprise from about 0.1% to about 1% by weight of an oxygen scavenger. In a still further aspect, the compositions comprise from about 0.1% to about 5% by weight of an oxygen scavenger. In an even further aspect, the compositions comprise from about 3% to about 10% by weight of an oxygen scavenger. In a still further aspect, embodiment the compositions comprise from about 5% to about 10% by weight of an oxygen scavenger. In a yet further aspect, the compositions comprise from about 2% to about 7% by weight of an oxygen scavenger.

In various aspects, the disclosed compositions comprise a base polymer. In a further aspect, the base polymer can comprise one or more homopolymers or copolymers as described herein. In one aspect, the compositions can comprise from about 80% to about 99.98% by weight of a base polymer. In a further aspect, the composition comprises from about 80% to about 99% by weight of a base polymer. In a still further aspect, the composition comprises from about 85% to about 99% by weight of a base polymer. In a yet further aspect, the composition comprises from about 90% to about 99.98% by weight of a base polymer. In an even further embodiment the composition comprises from about 95% to about 99% by weight of a base polymer. In a still further aspect, the composition comprises from about 95% to about 99.98% by weight of a base polymer. In a yet further aspect, the composition comprises from about 97% to about 99% by weight of a base polymer.

In a further aspect, a variety of different polymers can be used as the base polymer. The disclosed compositions enable oxygen scavenging, and thus the base polymer generally includes those polymers that can be subject to oxidation. For example, polymers that exhibit at least some oxygen permeability are useful with the disclosed compositions, at least inasmuch as the disclosed compositions can reduce the oxidative damage to the polymer.

In a further aspect, the base polymer can be a polymer commonly used in packaging materials including polyethylene, such as low density polyethylene, very low density polyethylene, ultra-low density polyethylene, high density polyethylene, and linear low density polyethylene; polyesters such as (PET), (PEN) and their copolymers such as PET/IP; polyvinyl chloride (PVC); polyvinylidene chloride (PVDC); and ethylene copolymers such as ethylene/vinyl acetate copolymer, ethylene/alkyl (meth)acrylate copolymers, ethylene/(meth)acrylic acid copolymers, and ionomers. Blends of different base polymers also can be used.

In a further aspect, the base polymer can include one or more polymers approved by the U.S. Food and Drug Administration (FDA). Non-limiting examples include polyethylene terephthalate, polypropylene, and polyethylene.

In a further aspect, the base polymer comprises a polyester polymer or copolymer. Preferred polyesters include polymers of phthalic acids, such as polyethylene terephthalate (PET), or a copolymer thereof. PET, for example, can be made from terephthalic acid and ethylene glycol. PET can also be made using dimethyl terephthalate and ethylene glycol. Preferred copolymers of phthalic acids include copolymers of a phthalic acid and one or more hydroxylated organic compounds. Examples of suitable hydroxylated organic compounds include 1,4-cyclohexandedimethanol, 1,2-propanediol, 1,4-butanediol, 2,2-dimethyl-1,3-propanediol, 2-methyl-1,3-propanediol (2MPDO), 1,6-hexanediol, 1,2-cyclohexanediol, 1,4-cyclohexanediol, 1,2-cyclohexanedimethanol, 1,3-cyclohexanedimethanol, and diols containing one or more oxygen atoms in the chain, e.g., diethylene glycol, triethylene glycol, dipropylene glycol, tripropylene glycol, or mixtures of these, and the like.

In a further aspect, the base polymer includes a polyethylene terephthalate homopolymer and copolymer modified with one or more polycarboxylic acid modifiers in a cumulative amount of less than about 15 mole %, or about 10 mole % or less, or about 8 mole % or less, or one or more hydroxyl compound modifiers in an amount of less than about 60 mol %, or less than about 50 mole %, or less than about 40 mole %, or less than about 15 mole %, or about 10 mole % or less, or about 8 mole % or less and polyethylene naphthalate homopolymers and copolymers modified with a cumulative amount of less than about 15 mole %, or about 10 mole % or less, or about 8 mole % or less, of one or more polycarboxylic acid modifiers or modified with less than about 60 mol %, or less than about 50 mole %, or less than about 40 mole %, or less than about 15 mole %, or about 10 mole % or less, or about 8 mole % or less of one or more hydroxyl compound modifiers, and blends thereof. In some aspects, the base polymer comprises at least 90 mole %, 92 mole %, or 94 mole % ethylene terephthalate repeat units based on the moles of all repeat units in the polyester polymers.

Polyesters such as PET can be prepared by polymerization procedures known in the art sufficient to effect esterification and polycondensation. Polyester melt phase manufacturing processes include direct condensation of a dicarboxylic acid with a diol, optionally in the presence of one or more esterification catalysts, in the esterification zone, followed by polycondensation in the prepolymer and finishing zones in the presence of a polycondensation catalyst; or ester exchange usually in the presence of a transesterification catalyst in the ester exchange zone, followed by prepolymerization and polymerization in the presence of a polycondensation catalyst.

As briefly discussed above, the disclosed compositions can comprise a transition metal in a positive oxidation state. The transition metal enhances the oxygen scavenging properties of the oxygen scavenger compound. Amounts of transition metal in the composition can be greater than zero and can be up to 5000 ppm. Generally, the transition metal will be present in an amount of from about 10 ppm to about 400 ppm. In one aspect, about 200 ppm of the transition metal is present. In a further aspect, about 250 ppm of the transition metal is present. In wall applications (as opposed to master batch applications where more transition metal is used), it can be preferred to keep the level of metal below 300, more preferably 250 ppm. In a further aspect, the transition metal is present from 30 to 150 ppm. In a further aspect, about 50 ppm of the transition metal is present. In a further aspect, about 100 ppm of the transition metal is present. In a further aspect, about 150 ppm of the transition metal is present.

In a further aspect, the transition metal can be a transition metal from the first, second, or third transition series of the Periodic Table. The metal can be Rh, Ru, or one of the elements in the series of Sc to Zn (e.g., Sc, Ti, V, Cr, $M_n$, Fe, Co, Ni, Cu, and Zn). In one aspect, the transition metal is cobalt. Cobalt can be used in +2 or +3 oxidation states. In some aspects, it is preferred to use cobalt in the +2 oxidation state. In a further aspect, the transition metal is rhodium. For example, rhodium in the +2 oxidation state can be used. The transition metal can also be a positive oxidation form of zinc.

In a further aspect, the transition metal can be present as a salt. The cation of the salt can be the transition metal in a positive oxidation state. A variety of anions can stabilize the positively charged transition metal. Suitable anions for the salts include, but are not limited to, chloride, acetate, oleate, stearate, palmitate, 2-ethylhexanoate, carboxylates, such as neodecanoates, octanoates, acetates, lactates, naphthalates, malates, stearates, acetylacetonates, linoleates, oleates, palmitates, 2-ethylhexanoates, or ethylene glycolates; or as their oxides, borates, carbonates, dioxides, hydroxides, nitrates, phosphates, sulfates, or silicates, among others. Representative transition metal salts include cobalt (II) 2-ethylhexanoate, cobalt oleate, and cobalt (II) neodecanoate. The transition metal salt also can be an ionomer, in which case a polymeric counter ion can be present.

In a further aspect, the composition can comprise a colorant in a visually effective amount. A visually effective amount refers to an amount of colorant that results in the composition or an article made therefrom appear colored to the naked eye. A composition comprising a visually effective amount of colorant can refer to a composition having at least 0.01% by weight colorant. In a further aspect, the composition can comprise at least 0.25% by weight colorant. In a still further aspect, the composition can comprise at least 0.5% by weight colorant. The compositions can also comprise up to or even exceed about 3% by weight colorant.

A visually effective amount can be determined, for example, by performing a spectrophotometric scan of the composition or article using a wavelength range from 400 to 700 nm (visible region). Specific colors can be characterized according to their spectral pattern. Every color also has its own characteristic L (lightness gradation), a (red to green) and b (yellow to blue) numbers, which can be used to characterize the compositions and articles.

The colorant can be a variety of pigments and dyes, many of which are commercially available. Examples of colorants include without limitation COLORMATRIX Dark Amber, product code: 189-10034-6, COLORMATRIX Dead Leaf Green, product codes: 284-2801-3 and 84-2801-1, AMER-ICHEM amber, product code: 59108-CD1, Champaigne green, and COLORMATRIX amber, product code: 189-10100-1.

In various aspects, the composition can include other components such as fillers, crystallization aids, impact modifiers, surface lubricants, denesting agents, stabilizers, ultraviolet light absorbing agents, metal deactivators, nucleating agents such as polyethylene and polypropylene, phosphate stabilizers and dyestuffs. Typically, the total quantity of such components will be less than about 10% by weight of the composition. In some embodiments, the amount of these optional components is less than about 5% by weight of the composition.

In a further aspect, the composition can comprise a reheat additive. Reheat additives are commonly used in the manufacture of polyester polymer compositions used to make stretch blow molded bottles because the preforms made from the composition must be reheated prior to entering the mold for stretch blowing into a bottle. Any conventional reheat additive can be used, such as various forms of black particles, e.g., carbon black, activated carbon, black iron oxide, glassy carbon, silicon carbide, gray particles such as antimony, and other reheat additives such as silicas, red iron oxide, and the like.

In a further aspect, the composition can also comprise an impact modifier. Examples of typical impact modifiers useful in the composition include ethylene/acrylate/glycidyl terpolymers and ethylene/acrylate copolymers in which the acrylate is a methyl or ethyl acrylate or methyl or ethyl methacrylate or the corresponding butyl acrylates, styrene based block copolymers, and various acrylic core/shell type impact modifiers. The impact modifiers can be used in conventional amounts from about 0.1 to about 25 weight percent of the overall composition and, in some aspects, in amounts from about 0.1 to about 10 weight percent of the composition.

In many applications, not only are the packaging contents sensitive to the ingress of oxygen, but the contents may also be affected by UV light. Fruit juices and pharmaceuticals are two examples of such contents. Accordingly, in some aspects, it is desirable to incorporate into the composition a UV absorbing compound in an amount effective to protect the packaged contents.

In a further aspect, the disclosed composition or an article made therefrom can have an Oxygen Transmission Rate (OTR) of less than about 0.1 (units of cc/pkg/day or 1-5 cc-mm/mg-day-atm) under standard conditions. In a further aspect, the OTR can be less than 0.03, less than 0.01, less than 0.005, or less than 0.001. The OTR is a measure of how well the oxygen scavenger compound functions at scavenging oxygen that permeates the composition or article.

When OTR is expressed for a given composition or article, the units "cc/package/day" ("cc/pkg/day") are typically employed. The term package refers to a barrier between an atmosphere of relatively lower oxygen content and an atmosphere of relatively higher oxygen content. Typical barriers (e.g., packages) include bottles, thermoformed containers, and films (e.g., shrink wrap).

Oxygen Transmission Rate (oxygen permeation) can be measured, for example, as described in U.S. Pat. No. 5,021,515. A material of area A can be exposed to a partial pressure p of oxygen on the one side and to an essentially zero partial pressure of oxygen on the other side. The quantity of oxygen emerging on the latter side is measured and expressed as a volume rate dV/dt, the volume being converted to some standard condition of temperature and pressure. After a certain time of exposure (usually a period of a few days) dV/dt is generally found to stabilize, and a $P_W$ value can be calculated from equation below:

$$dV/dt = P_W A p \qquad (1)$$

$P_W$ refers to the permeance of the wall. (Analogy with magnetic permeance and electrical conductance would suggest that $P_W$ should be described as "permeance per unit area", but we are following the nomenclature in Encyclopedia of Polymer Science and Technology, Vol. 2, Wiley Interscience, 1985, page 178.) The standard conditions for expressing dV/dt are 0° C. and 1 atm (1 atm=101 325 $Nm^{-2}$). If the thickness of the area of wall is substantially constant over the area A with value T and the wall is uniform through the thickness (i.e., the wall is not a laminated or coated one) then the permeability of the material in the direction normal to the wall is calculated from the equation below.

$$dV/dt = P_M A p / T \qquad (2)$$

For non-scavenging materials, $P_W$ and $P_M$ are to a reasonable approximation independent of t and p, and $P_M$ of T although they are often appreciably dependent on other conditions of the measurement such as the humidity of the atmosphere on the oxygen-rich side and the temperature of the measurement.

For oxygen-scavenging walls, $P_W$ and $P_M$ are functions of t because the concentrations and activity of scavenger vary with time (particularly as the scavenger is consumed). This typically does not prevent measurement of $P_W$ and $P_M$ reasonably accurately as a function of time, because the changes in dV/dt are relatively gradual once the normal initial equilibration period of a few days is over. After a few days' exposure to the measurement conditions, however, a non-scavenging material typically achieves a steady state in which dV/dt is equal to the rate of oxygen ingress to the wall, while a scavenging material achieves an (almost) steady state in which dV/dt is considerably less than the rate of oxygen ingress to the material. This being the case, it is likely that $P_W$ calculated from (1) is a function of p as well as of t and that $P_M$ in (2) is a function of p and T as well as of t. $P_W$ and $P_M$ for scavenging materials are, strictly speaking, not true permeances and permeabilities at all (since permeation and scavenging are occurring simultaneously) but, rather, apparent ones.

Values of $P_W$ and $P_M$ (except where stated otherwise) are to be understood to refer to conditions in which p=0.21 atm, the relative humidity on the oxygen-rich side of the wall is 50%, the temperature is 23° C. and (in the case of $P_M$ values) the thickness of the material of about 0.45 mm. Conditions close to the first three of these, at least, are conventional in the packaging industry.

For example, OTR can be measured for bottles, for example, by controlling the atmosphere on both sides of a sample of bottles and measuring the rate of oxygen permeation over time. Typically, the bottles are mounted on a plate such that there are two ports for gas inlet and outlet. The interior of the bottles is separated from the exterior by an air tight seal. After sealing, the interior of the bottle is flushed with N₂ gas (or N₂+H₂ mixture) to remove any oxygen present before mounting on plate. The bottle is then placed in a controlled environmental chamber (maintained at 23° C. and 50% RH) such that the exterior of the bottle is at standard atmosphere with ~21% oxygen. The interior of the bottle is continuously flushed with N₂ (or N₂+H₂) at a known gas flow rate. The outlet of the flushed gases contains oxygen permeating through the bottle wall. This flushed gas from the bottle interior is passed over a sensor that is calibrated to measure oxygen content of the flushed gas. Such measurements of oxygen content are made continuously over time until a steady state is reached. This steady state value is typically reported as Oxygen Transmission Rate (OTR) for that bottle in the units of cc/package/day. A preferred OTR for PET bottles is less than 0.1 cc/package/day; more preferred is less than 0.01 cc/package/day; most preferred for PET bottles is less than 0.001 cc/package/day over the shelf life of the packaged product.

In one aspect, a disclosed composition has an OTR of less than that of an otherwise identical composition in the absence of the oxygen scavenger compound and the transition metal. In a further aspect, a disclosed composition has an OTR of less than about 75%, less than about 50%, less than about 25%, less than about 20%, less than about 10%, less than about 5%, or less than about 1% of an otherwise identical composition in the absence of the oxygen scavenger compound and the transition metal.

In one aspect, the invention provides oxygen scavenging compositions that react with oxygen in the presence of transition metals and salts thereof, comprising, an effective amount of a disclosed oxygen scavenger compound.

In a further aspect, the invention provides oxygen scavenging compositions that react with oxygen in the presence of transition metals and salts thereof, comprising, an effective amount of a compound of Formula (I)-(IV).

In a further aspect, the invention provides an oxygen scavenging system comprising: (a) an oxygen scavenging composition, comprising a compound of Formula (I)-(IV); (b) an effective amount of a transition metal catalyst; and (c) a functional barrier permeable to oxygen.

In a further aspect, the invention also relates to organic material normally susceptible to gradual degradation in the presence of oxygen during use over an extended period containing an antioxidant effective, or oxygen scavenging effective amount of a disclosed oxygen scavenger compound.

In a further aspect, the invention also relates to organic material normally susceptible to gradual degradation in the presence of oxygen during use over an extended period containing an antioxidant effective, or oxygen scavenging effective amount of a compound of Formula (I)-(IV).

C. Methods

In various aspects, the invention relates to methods for making the disclosed compounds. In a further aspect, oxygen scavengers of the present invention can be synthesized by reacting excess meta-xylylenediamine (MXDA) with phthalide under conditions effective to produce the desired product, as depicted below:

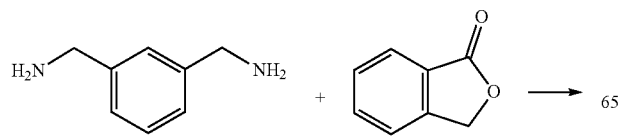

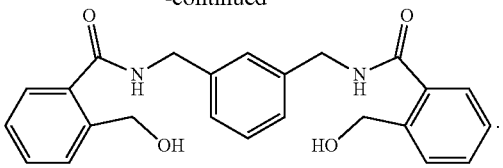

In some aspects, the hydroxymethyl substituent can be para- to the amide functionality. In a further aspect, p-MXBH can be synthesized by reacting 1,4-benzenedimethanol, potassium tert-butoxide, and meta-xylenediamine in the presence of a N-heterocyclic carbene based ruthenium-catalyst under conditions effective to provide the desired compound. For example, in a still further aspect, about 20 mmol of 1,4-benzenedimethanol, about 3 mmol potassium tert-butoxide, and about 0.6 mmol of N-heterocyclic carbene based ruthenium-catalyst are dissolved in 500 mL of toluene and heated to reflux while vigorous stirring is maintained. In an even further aspect, about 10 mmol of meta-xylene diamine is added dropwise into the solution slowly, and the reflux and stirring are maintained for another 24 h. At the end of the reaction, toluene is distilled off to obtain the crude product, which is purified, for example, by chromatography over silica gel, to produce p-MXBH, represented by the structure below:

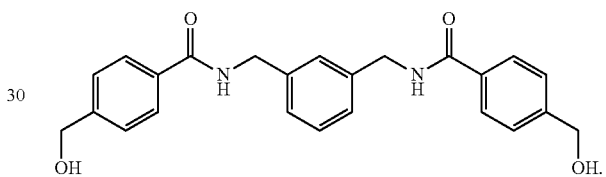

In some aspects, the hydroxymethyl substituent can be meta- to the amide functionality. In a further aspect, m-MXBH can be synthesized by reacting mono-methyl isophthalate, 1-ethyl-3-(3-dimethylaminopropyl) carbodiimide hydrochloride, 1-hydroxy-7-azabenzotriazole, 4-dimethylaminopyridine, m-xylenediamine, and N,N-diisopropylethylamine under conditions effective to provide the desired compound. For example, in a still further aspect, to a solution of 2.0 mmol mono-methyl isophthalate, 1-ethyl-3-(3-dimethylaminopropyl) carbodiimide hydrochloride (0.77 g, 4.0 mmol), 1-hydroxy-7-azabenzotriazole (0.41 g, 3.0 mmol) and 4-dimethylaminopyridine (0.25 g, 2.0 mmol) in anhydrous dichloromethane (DCM, 10 mL) can be added m-xylenediamine (0.18 mL, 1.5 mmol) and N,N-diisopropylethylamine (1.05 mL, 6.03 mmol). In a yet further aspect, the reaction mixture can then be stirred for a sufficient duration, washed with 10% aqueous citric acid, and extracted twice with DCM. The organic layer can then be washed with saturated aqueous sodium bicarbonate, brine, dried over Na₂SO₄ and concentrated in vacuo. The residue can then be purified, for example, by chromatography over silica gel, to produce m-MXBH, represented by the structure below:

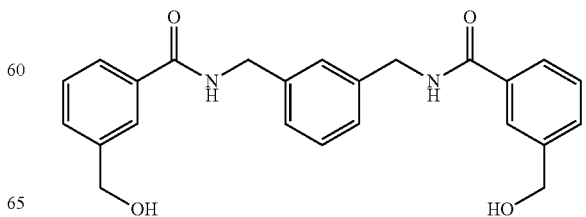

In various aspects, the disclosed oxygen scavengers can have additional substituents. In a further aspect, Cl—NBHB (N-benzyl-2-(hydroxymethyl)benzamide) can be synthesized by reacting mono-methyl isophthalate, 1-ethyl-3-(3-dimethylaminopropyl) carbodiimide hydrochloride, 1-hydroxy-7-azabenzotriazole, 4-dimethylaminopyridine, m-xylenediamine, and N,N-diisopropylethylamine under conditions effective to provide the desired compound. For example, in a still further aspect, to a solution of 2.0 mmol mono-methyl isophthalate, 1-ethyl-3-(3-dimethylaminopropyl) carbodiimide hydrochloride (0.77 g, 4.0 mmol), 1-hydroxy-7-azabenzotriazole (0.41 g, 3.0 mmol) and 4-dimethylaminopyridine (0.25 g, 2.0 mmol) in anhydrous dichloromethane (DCM, 10 mL) can be added 3-chlorobenzylamine (0.37 mL, 3.0 mmol) and N,N-diisopropylethylamine (1.05 mL, 6.03 mmol). In a yet further aspect, the reaction mixture can then be stirred for a sufficient duration, washed with 10% aqueous citric acid, and extracted twice with DCM. The organic layer can then be washed with saturated aqueous sodium bicarbonate, brine, dried over Na$_2$SO$_4$ and concentrated in vacuo. The residue can then be purified, for example, by chromatography over silica gel, to produce Cl—NBHB, represented by the structure below:

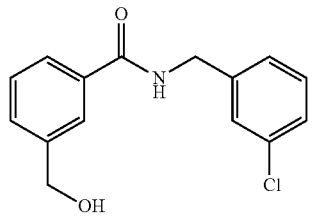

In various aspects, the disclosed oxygen scavengers can also have other tethering groups comprising other heteroatoms, for example and without limitations, N or S. In a further aspect, 4-(aminomethyl)-N-benzylbenzamide can be synthesized by the following procedure. In a still further aspect, 15 g (100 mmol) of 4-aminomethylbenzoic acid suspended in 150 ml of water can be mixed with 30 g of potassium carbonate, and 28 mL (120 mmol) of di-tert-butyl carbonate can be added dropwise under cooling with ice. The reaction solution can then be stirred at 40° C. for 3 hours and at room temperature overnight. After addition of 50 mL of water and 40 g of citric acid, the precipitated crystals can be collected by filtration, washed with 50 mL of water and dried under reduced pressure. The crystals can then be suspended in 600 mL of methylene chloride stirred at room temperature with 24 g (150.0 mmol) of carbonylbisimidazole (CDI) for 40 minutes and then with 30.0 mL (0.3 mol) of benzylamine overnight. The reaction solution can then be separated between 600 mL of saturated aqueous sodium hydrogen carbonate and 900 mL of methylene chloride, and the organic layer washed with 600 mL of saturated aqueous sodium chloride, dried over anhydrous sodium sulfate and filtered. The filtrate can then be concentrated under reduced pressure. The resulting residue can then be dissolved in 150 mL of methylene chloride and 150 mL of methanol and concentrated with 90 g of silica gel under reduced pressure and purified by chromatography. The intermediate obtained can then be dissolved in 600 mL of 1,4-dioxane and stirred with 600 mL of 4 M hydrochloric acid/1,4-dioxane at room temperature for 17 hours and concentrated under reduced pressure to obtain the desire product, represented by the structure:

Further embodiments of the present invention can be prepared using methods and modifications known generally in the art.

In a further aspect, the invention relates to methods for making oxygen scavenging polymers. In a still further aspect, the method comprises the steps of: a) providing a monomer comprising a moiety represented by the formula:

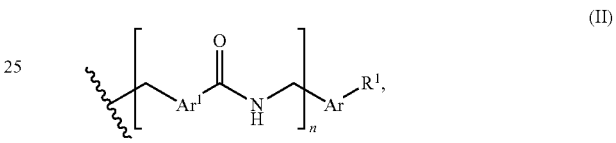

(II)

wherein n is 2, 3, 4, 5, or 6; wherein Ar is aryl or heteroaryl; wherein Ar$^1$ is aryl or heteroaryl; and wherein Ar$^1$ is substituted with 0, 1, 2, or 3 groups independently selected from halogen, C1-C4 alkyl, electron withdrawing groups, and electron donating groups, and valence is satisfied; and wherein R$^1$ represents 6-n groups independently selected from hydrogen, halogen, C1-C4 alkyl, electron withdrawing groups, and electron donating groups; and b) subjecting the monomer to conditions effective to provide the oxygen scavenging polymer.

In a yet further aspect, conditions effective to provide comprise polymerization of polyethylene terephthalate. In a still further aspect, conditions effective to provide comprise providing or introducing the monomer during the polymerization of polyethylene terephthalate. In an even further aspect, the oxygen scavenging polymer has the structure:

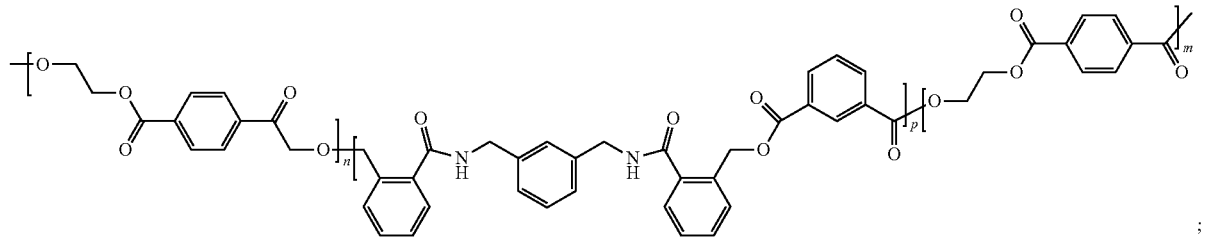

;

wherein m is an integer 1 or greater; wherein n is an integer 1 or greater; and wherein p is an integer 1 or greater. For example, m can be from 1 to about 10,000, or from 1 to about 1,000, or from 1 to about 100. In a further aspect, n can be from 1 to about 10,000, or from 1 to about 1,000, or from 1 to about 100. In a still further aspect, p can be from 1 to about 1,000, or from 1 to about 100.

In another aspect, an oxygen scavenging polymer of the present invention can be synthesized by heating and stirring MXBH and stoichiometric amount of di-acid, either neat or dissolved in a solvent, for example xylene, to a sufficiently high temperature inside a flask equipped with a Dean-Stark trap. In a further aspect, the water condensate can then be removed from the Dean-Stark trap, which drives the reaction forward. The reaction completes when water no longer forms.

In a further aspect, the invention also relates to a method of making an oxygen scavenging polymer comprising the step of: functionalizing polyethylene terephthalate with a moiety represented by the formula:

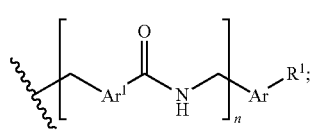
(II)

wherein n is 2, 3, 4, 5, or 6; wherein Ar is aryl or heteroaryl; wherein $Ar^1$ is aryl or heteroaryl; and wherein $Ar^1$ is substituted with 0, 1, 2, or 3 groups independently selected from halogen, C1-C4 alkyl, electron withdrawing groups, and electron donating groups, and valence is satisfied; and wherein $R^1$ represents 6-n groups independently selected from hydrogen, halogen, C1-C4 alkyl, electron withdrawing groups, and electron donating groups.

In another aspect, an oxygen scavenging polymer of the present invention can be synthesized by mixing PET oligomers/polymers with oligomers of Formula (III-IV) in a melt-condensation or solid-state condensation reactor under typical condensation reaction conditions under vacuum.

In a further aspect, the invention also relates to methods for making the disclosed compositions. Various methods exist for making the disclosed compositions. In one aspect, the composition can be made by mixing the base polymer with the oxygen scavenger compound and optionally the transition metal. In some aspects, some or part of the transition metal may already be present in the base polymer prior to mixing, for example if the transition metal is used as a catalyst for making the base polymer. In some aspects, the base polymer, the oxidizable organic component or oxygen scavenger and the transition metal are mixed by tumbling in a hopper. Other optional ingredients can be added during this mixing process or added to the mixture after the aforementioned mixing or to an individual component prior to the aforementioned mixing step.

When melt processing is desired for the composition, the composition can also be made by adding each ingredient separately and mixing the ingredients just prior to melt processing the composition to form an article. In some embodiments, the mixing can be just prior to the melt process zone. In other embodiments, one or more ingredients can be premixed in a separate step prior to bringing all of the ingredients together.

In some aspects, the transition metal can be added neat or in a carrier (such as a liquid or wax) to an extruder or other device for making the article, or the metal can be present in a concentrate or carrier with the oxygen scavenger compound, in a concentrate or carrier with the base polymer, or in a concentrate or carrier with a base polymer/oxygen scavenger compound blend. It is desirable that the addition of the transition metal does not substantially increase the intrinsic viscosity of the melt in the melt processing zone. Thus, transition metal or metals can be added in two or more stages, such as once during the melt phase for the production of the base polymer and again once more to the melting zone for making the article.

The melt blend of base polymer, oxygen scavenger compound, and transition metal catalyst can also be prepared by adding the components at the throat of an injection molding machine that: (i) produces a preform that can be stretch blow molded into the shape of the container, (ii) produces a film that can be oriented into a packaging film, (iii) produces a sheet that can be thermoformed into a food tray, or (iv) produces an injection molded container. The mixing section of the extruder should be of a design to produce a homogeneous blend. Such process steps work well for forming carbonated soft drink, water or beer bottles, packaging films and thermoformed trays. The present invention can be employed in any of the conventional known processes for producing a polymeric container, film, tray, or other article that would benefit from oxygen scavenging.

According to further aspects of the disclosure, the invention provides methods for packaging an oxygen sensitive material, comprising: (a) preparing a package having a wall comprising at least one layer, at least one of the layers comprising a composition, the composition, comprising: (i) a base polymer; (ii) at least one compound of Formula (I)-(IV); and (iii) at least one transition metal in a positive oxidation state, the metal being present in the composition in an amount of 10 to 400 ppm; wherein the compound is present in an amount of about 0.10 to 10 weight percent of the composition; (b) introducing the oxygen sensitive material into the package; and (c) closing the package.

D. Articles

In further aspects, the present invention also relates to articles comprising the disclosed compounds and compositions. Various articles can be prepared from the disclosed compositions. Thus, the articles prepared from the compositions will also have the composition present in the article. Suitable articles include vessels and films, such as flexible sheet films, flexible bags, pouches, semi-rigid and rigid containers such as bottles (e.g. PET bottles) or metal cans, or combinations thereof. Typical flexible films and bags include those used to package various food items and can be made up of one or a multiplicity of layers to form the overall film or bag-like packaging material. The composition of the present invention can be used in one, some or all of the layers of such packaging material.

Specific articles include preforms, containers and films for packaging of food, beverages, cosmetics, pharmaceuticals, and personal care products where a high oxygen barrier is needed. Examples of beverage containers are bottles for holding water and carbonated soft drinks, and the invention is particularly useful in bottle applications containing juices, sport drinks, beer or any other beverage where oxygen detrimentally affects the flavor, fragrance, performance (e.g., vitamin degradation), or color of the drink. The compositions are also particularly useful as a sheet for thermoforming into rigid packages and films for flexible structures. Rigid packages include food trays and lids. Examples of food tray applications include dual oven able food trays, or cold storage food trays, both in the base container and in the lidding (whether a thermoformed lid or a film), where the freshness of the food contents can decay with the ingress of oxygen. The compositions can also be used in the manufacture of cosmetic containers and containers for pharmaceuticals or medical devices.

Other suitable articles include rigid or semi-rigid articles including plastic, such as those utilized for juices, soft drinks, as well as thermoformed trays or cup normally having thickness in the range of from 100 to 1000 micrometers. The walls of such articles can comprise single or multiple layers of materials. The article can also take the form of a bottle or can, or a crown, cap, crown or cap liner, plastisol or gasket. The composition of the present invention can be used as an integral layer or portion of, or as an external or internal coating or liner of, the formed semi-rigid or rigid packaging article. As a liner, the composition can be extruded as a film along with the rigid article itself, e.g., by coextrusion, extrusion coating, or an extrusion lamination process, so as to form the liner in situ during article production; or alternatively can be adhered by heat and/or pressure, by adhesive, or by any other suitable method.

In a further aspect, the disclosed compositions can be used for forming a layer of a wall which primarily provides oxygen-scavenging (another layer including polymer providing gas barrier without significant scavenging), or as a head-space scavenger (completely enclosed, together with the package contents, by a package wall). When the compositions are used in a wall or as a layer of a wall, the permeability of the composition for oxygen is advantageously not more than about 3.0, or about 1.7, or about 0.7, or about 0.2, or about 0.03 $cm^3$-mm/($m^2$-atm-day). In some aspects, the permeability of the composition is not more than about three-quarters of that in the absence of the oxygen scavenger compound. In other aspects, the permeability is not more than about one half, one-tenth in certain embodiments, one twenty-fifth in other embodiments, and not more than one-hundredth of that in the absence of the oxygen scavenger compound.

Although it can be preferable from the standpoint of packaging convenience and/or scavenging effectiveness to employ the present invention as an integral or discrete part of the packaging wall, the invention can also be used as a non-integral component of a packaging article such as, for example, a bottle cap liner, adhesive or non-adhesive sheet insert, sealant, sachet, fibrous mat insert or the like.

Besides articles applicable for packaging food and beverage, articles for packaging other oxygen-sensitive products can also benefit from the present invention. Such products would include pharmaceuticals, oxygen sensitive medical products, corrodible metals or products, electronic devices and the like.

In a further aspect, the composition can be used as a master batch for blending with a polymer or a polymer containing component. In such compositions, the concentration of the oxygen scavenger compound and the transition metal will be high enough to allow for the final blended product to have suitable amounts of these components. The master batch can also contain an amount of the base polymer with which the master batch is blended.

Oxygen permeability of an article can be maintained for a longer period of time by storing the article in a sealed container or under an inert atmosphere such as nitrogen prior to use with oxygen sensitive materials.

In one aspect, the invention provides containers comprising a film forming polymer, having at least one wall comprising an effective amount of an oxygen scavenging composition comprising a disclosed oxygen scavenger compound.

In a further aspect, the invention provides containers comprising a film forming polymer, having at least one wall comprising an effective amount of an oxygen scavenging composition comprising a compound Formula (I)-(IV).

In a further aspect, the invention provides package walls comprising at least one layer, the layer comprising a composition, the composition comprising: (a) a base polymer; (b) at least one compound of Formula (I)-(IV); and (c) at least one transition metal in a positive oxidation state, the metal being present in the composition in an amount of 10 to 400 ppm; wherein the compound is present in an amount of about 0.10 to 10 weight percent of the composition.

In a further aspect, the invention provides package walls, comprising a composition, the composition comprising: (a) one or more outer layers; and (b) one or more inner layers; wherein at least one of the inner or at least one of the outer layers comprises a composition comprising: (1) a base polymer; (2) at least one compound of formula (I)-(IV); and (3) at least one transition metal in a positive oxidation state, the metal being present in the composition in an amount of 10 to 400 ppm; wherein the compound is present in an amount of about 0.10 to 10 weight percent of the composition. In some aspects, the first layer is disposed radially outward from the second layer.

The articles can be made by various methods known in the art. Generally, the articles are prepared by melt processing methods (i.e., a melt of the composition). Such processes generally include injection molding, stretch blow molding, extrusion, thermoforming, extrusion blow molding, and (specifically for multilayer structures) coextrusion and lamination using adhesive tie layers. Orientation, e.g., by stretch blow molding, of the polymer can be used with phthalate polyesters because of the known mechanical advantages that result.

The melt processing zone for making the article can be operated under customary conditions effective for making the intended articles, such as preforms, bottles, trays, and other articles mentioned above. In one aspect, such conditions are effective to process the melt without substantially increasing the intrinsic viscosity of the melt and which are ineffective at promoting transesterification reactions. In some preferred aspects, suitable operating conditions effective to establish a physical blend of the base polymer, oxidizable organic component, and transition metal are temperatures in the melt processing zone within a range of about 250° C. to about 300° C. at a total cycle time of less than about 6 minutes, and typically without the application of vacuum and under a positive pressure ranging from about 0 psig (pound-force per square inch gauge) to about 900 psig. In some embodiments, the residence time of the melt on the screw can range from about 1 to about 4 minutes.

In one aspect, the invention provides methods for producing a packaging material having a wall with oxygen barrier properties comprising: (a) combining a base polymer with at least one compound of formula (I)-(IV) to form a composition, the composition having at least one transition metal in a positive oxidation state, the metal being present in the composition in an amount of 10 to 400 ppm; and wherein the compound is present in an amount of about 0.10 to 10 weight present of the composition; (b) forming the product of step (a) into a wall; and (c) forming a container which comprises the wall.

In a further aspect, the invention provides methods for making an article, comprising: (a) forming a melt by combining in a melt processing zone: (i) a base polymer; (ii) at least one compound of formula (I)-(IV), and (iii) at least one transition metal in a positive oxidation state, the metal being present in the composition in an amount of 10 to 400 ppm; wherein the compound is present in an amount of about 0.10 to 10 weight present of the composition; (b) forming an article from the melt.

E. Experimental

The following examples are put forth so as to provide those of ordinary skill in the art with a complete disclosure and description of how the compounds, compositions, articles, devices and/or methods claimed herein are made and evaluated, and are intended to be purely exemplary and are not intended to limit the disclosure. Efforts have been made to ensure accuracy with respect to numbers (e.g., amounts, temperature, etc.), but some errors and deviations should be accounted for. Unless indicated otherwise, parts are parts by weight, temperature is in ° C. or is at ambient temperature, and pressure is at or near atmospheric.

1. Example 1: Synthesis of m-Xylylenediamine-bis(2-(hydroxymethyl)benzamide)

In an exemplary synthetic example, excess amount of neat m-xylene diamine (MXDA) is stirred with phthalide at room temperature for overnight. The white precipitation is filtered and washed with water to yield m-xylylenediamine-bis(2-(hydroxymethyl)benzamide) (MXBH). This method requires large excess amount of MXDA (>10 fold excess) to drive the reaction to completion, although the excess MXDA can be reused in subsequent batches.

2. Example 2: Synthesis of m-Xylylenediamine-bis(2-(hydroxymethyl)benzamide)

In another exemplary synthetic example, 1.0 mL of MXDA and 1.9 g phthalide are dissolved in a mixture of 15 mL of EtOH and 0.5 mL of 10% aqueous NaOH solution, stirred at 50° C. for 3 h followed by stirring at room temperature for another 60 h. The dense white precipitation was filtered off and washed with water to yield MXBH of high purity.

3. Example 3: Synthesis of benzoic esters of m-Xylylenediamine-bis(2-(hydroxymethyl)benzamide)

In another exemplary synthetic example, 404 mg of MXBH, 244 mg of benzoic acid and a catalytic amount of antimony (III) oxide was added into 1 L of xylene in a flask equipped with a Dean Stark trap and a condenser. The suspension was heated to reflux and maintained, during which time water is collected in the Dean Stark trap. At the end of the reaction when no more water forms, xylene was distilled off under reduced pressure. The solid residue was dissolved in ethyl acetate, filtered and recrystallized in ethyl acetate-hexane to obtain pure product.

4. Example 4: Synthesis of polyethylene terephthalate with MXBH-ester Segments (Prophetic)

In another exemplary synthetic example, PET polymers with MXBH-ester segments can be prepared via normal PET synthesis processes from ethylene glycol and terephthalic acid over an appropriate catalyst (antimony (III) oxide, for example), using MXBH as an additive. MXBH can be introduced as an additive to either a melt-condensation reaction vessel or a solid state polycondensation reactor, or other reactive extrusion process. The product is expected to possess MXBH-ester oxygen scavenging segments embedded within PET chains. In one aspect, the end group of PET polymer, for example, —COOH, can react with the —OH end group of MXBH-ester segment to give off water, thereby extending the PET chain with MXBH-ester chain. In another aspect, an "ester exchange" reaction can take place, wherein the ester bond in PET breaks to create new end groups which can then react with MXBH-end groups. In a further aspect, it is believed the chain created from the ester exchange reaction will be shorter. In a still further aspect, the concentration of such segments can also depend upon the let-down ratio of the MXBH additive in the condensation reactions.

5. Example 5: Oxygen Scavenging Performance of MXBH in Polyethylene Terephthalate Oxygen scavenging performance of the oxygen scavenging compositions of the present invention in different resins were evaluated using Oxysense™. Oxygen Transmission Rate can be calculated from OxySense data. OxySense measurements were carried out in a sealed OxyVial with a Ruthenium dye-based sensitizer attached to the inside wall of the vial. Upon illumination at a specific wavelength, the sensitizer gives off luminescence the intensity of which is correlated with the concentration of the oxygen in the vial. As a result, a trace of oxygen concentration change as a function of time can be plotted. The tests can be performed at higher temperatures to speed up the tests.

Polymer compositions comprising the oxygen scavenger compound prepared in Example 1 [m-xylylenediamine-bis (2-(hydroxymethyl)benzamide) or MXBH] were prepared to evaluate oxygen scavenging performance. To a batch of 700 g of pre-dried PET resins (at 170° C. for 4 hours in a Piovan dryer), MXBH powder was dosed at either 1.4% (wt.) or 2.0% (wt.) let-down ratios, along with CoNDA Catalyst MasterBatch 250 at either 1.5% (wt.) or 2.5% (wt). Each polymer composition was mixed well and fed into a BOY 22 S injection molding machine to mold plaques. The BOY 22 S injection molder barrel temperatures during injection molding was 260° C. for both heating zones, and the injection pressure was ~700 psi. The mold was water cooled prior to testing. The inventive formulations were prepared according to the parameters provided in Table 1.

TABLE 1

| Test No. | Resin type | MXBH LDR | Catalyst (CoNDA) LDR |
| --- | --- | --- | --- |
| 1 | ParaStar 7000 | 1.4% | 1.5% |
| 2 | ParaStar 7000 | 1.4% | 2.5% |
| 3 | ParaStar 7000 | 2.0% | 1.5% |
| 4 | ParaStar 9000 | 1.4% | 1.5% |
| 5 | ParaStar 9000 | 1.4% | 1.5% |

Parastar 7000 is a PET resin available from Eastman Chemical Co., Kingsport, TN, USA.

As shown in FIG. 1, all of the representative formulations comprising MXBH exhibit oxygen scavenging activity.

It will be apparent to those skilled in the art that various modifications and variations can be made in the present invention without departing from the scope or spirit of the invention. Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. An article of manufacture comprising a composition comprising:
    (i) a base polymer;
    (ii) a compound having a structure represented by a formula:

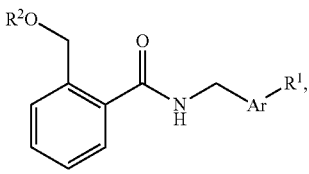

wherein Ar is aryl or heteroaryl;
wherein $R^1$ represents five groups independently selected from hydrogen, halogen, C1-C4 alkyl, electron withdrawing groups, electron donating groups, and a structure represented by a formula:

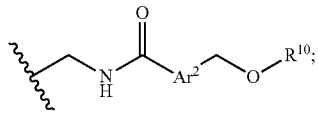

wherein $Ar^2$ is independently aryl or heteroaryl, and wherein $Ar^2$ is independently substituted with 0, 1, 2, or 3 groups independently selected from halogen, C1-C4 alkyl, electron withdrawing groups, and electron donating groups, and wherein valence is satisfied;
wherein $R^{10}$ is independently selected from hydrogen, C1-C4 alkyl, —C(O)$R^{20}$, and —C(O)$Ar^3$;
wherein $R^{20}$ is C1-C4 alkyl;
wherein each $Ar^3$ is phenyl or naphthyl, and wherein each $Ar^3$ is independently substituted with 0, 1, 2, or 3 groups independently selected from halogen, C1-C4 alkyl, —CO$_2R^{30}$, electron withdrawing groups, and electron donating groups, and wherein valence is satisfied;
wherein $R^{30}$, when present, is selected from hydrogen, C1-C4 alkyl, —(CH$_2$)$_n$OH, and —CH$_2Ar^4$;
wherein n is an integer selected from 1 or 2;
wherein $Ar^4$, when present, is aryl substituted with 0, 1, 2, and 3 groups selected from halogen, C1-C4 alkyl, and —C(O)NHCH$_2Ar^5$;
wherein each $Ar^5$, when present, is aryl substituted with 0, 1, 2, or 3 groups independently selected from halogen, C1-C4 alkyl, electron withdrawing groups, electron donating groups, and a structure represented by a formula:

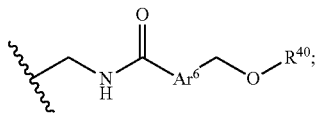

wherein each $R^{40}$, when present, is independently selected from hydrogen, C1-C4 alkyl, electron withdrawing groups, and electron donating groups;
wherein each $Ar^6$, when present, is aryl substituted with 0, 1, 2, and 3 groups independently selected from hydrogen, C1-C4 alkyl, electron withdrawing groups, and electron donating groups;

wherein $R^2$ is independently selected from hydrogen, C1-C4 alkyl, —C(O)$R^{50}$, and —C(O)$Ar^7$;
wherein $R^{50}$ is C1-C4 alkyl;
wherein each $Ar^7$ is aryl substituted with 0, 1, 2, and 3 groups independently selected from hydrogen, C1-C4 alkyl, and electron withdrawing groups, and electron donating groups, and valence is satisfied; and
(iii) at least one transition metal in a positive oxidation state.

2. A method of making an oxygen scavenging polymer comprising the steps of:
(a) providing a monomer comprising a moiety represented by a formula:

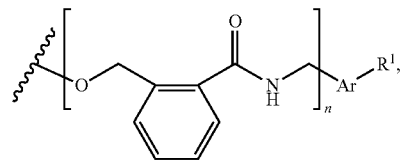

wherein n is 2, 3, 4, 5, or 6;
wherein Ar is aryl or heteroaryl;
wherein $R^1$ represents 6-n groups independently selected from hydrogen, halogen, C1-C4 alkyl, electron withdrawing groups, and electron donating groups; and
(b) polymerizing polyethylene terephthalate in the presence of the monomer, or functionalizing polyethylene terephthalate with the monomer.

3. The method of claim 2, wherein the method comprises polymerizing polyethylene terephthalate in the presence of the monomer.

4. The method of claim 2, wherein the method comprises functionalizing polyethylene terephthalate with the monomer.

5. A wall of a package comprising at least one layer, said layer comprising a composition comprising:
(i) a base polymer;
(ii) a compound having a structure represented by a formula:

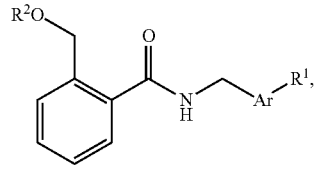

wherein Ar is aryl or heteroaryl;
wherein $R^1$ represents five groups independently selected from hydrogen, halogen, C1-C4 alkyl, electron withdrawing groups, electron donating groups, and a structure represented by a formula:

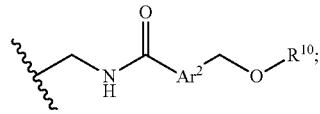

wherein Ar² is independently aryl or heteroaryl, and wherein Ar² is independently substituted with 0, 1, 2, or 3 groups independently selected from halogen, C1-C4 alkyl, electron withdrawing groups, and electron donating groups, and wherein valence is satisfied;

wherein $R^{10}$ is independently selected from hydrogen, C1-C4 alkyl, —C(O)R²⁰, and —C(O)Ar³;

wherein $R^{20}$ is C1-C4 alkyl;

wherein each Ar³ is phenyl or naphthyl, and wherein each Ar³ is independently substituted with 0, 1, 2, or 3 groups independently selected from halogen, C1-C4 alkyl, —CO₂R³⁰, electron withdrawing groups, and electron donating groups, and wherein valence is satisfied;

wherein $R^{30}$, when present, is selected from hydrogen, C1-C4 alkyl, —(CH₂)ₙOH, and —CH₂Ar⁴;

wherein n is an integer selected from 1 or 2;

wherein Ar⁴, when present, is aryl substituted with 0, 1, 2, and 3 groups selected from halogen, C1-C4 alkyl, and —C(O)NHCH₂Ar⁵;

wherein each Ar⁵, when present, is aryl substituted with 0, 1, 2, or 3 groups independently selected from halogen, C1-C4 alkyl, electron withdrawing groups, electron donating groups, and a structure represented by a formula:

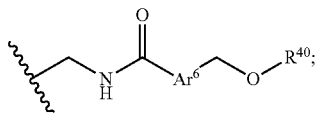

wherein each $R^{40}$, when present, is independently selected from hydrogen, C1-C4 alkyl, electron withdrawing groups, and electron donating groups;

wherein each Ar⁶, when present, is aryl substituted with 0, 1, 2, and 3 groups independently selected from hydrogen, C1-C4 alkyl, electron withdrawing groups, and electron donating groups;

wherein $R^2$ is independently selected from hydrogen, C1-C4 alkyl, —C(O)R⁵⁰, and —C(O)Ar⁷;

wherein $R^{50}$ is C1-C4 alkyl;

wherein each Ar⁷ is aryl substituted with 0, 1, 2, and 3 groups independently selected from hydrogen, C1-C4 alkyl, and electron withdrawing groups, and electron donating groups, and valence is satisfied; and (iii) at least one transition metal in a positive oxidation state.

6. The wall of claim 5, wherein said wall comprises (a) one or more outer layers; and (b) one or more inner layers;

wherein at least one of said inner or at least one of said outer layers comprises the composition.

* * * * *